(12) United States Patent
Tian et al.

(10) Patent No.: US 7,033,810 B2
(45) Date of Patent: Apr. 25, 2006

(54) SITOSTEROLEMIA SUSCEPTIBILITY GENE (SSG): COMPOSITIONS AND METHODS OF USE

(75) Inventors: Hui Tian, Foster City, CA (US); Joshua Schultz, Half Moon Bay, CA (US); Bei Shan, Redwood City, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 09/837,992

(22) Filed: Apr. 18, 2001

(65) Prior Publication Data

US 2002/0081687 A1 Jun. 27, 2002

Related U.S. Application Data

(60) Provisional application No. 60/198,465, filed on Apr. 18, 2000, and provisional application No. 60/204,234, filed on May 15, 2000.

(51) Int. Cl.
| | |
|---|---|
| *C21N 9/16* | (2006.01) |
| *C21N 1/20* | (2006.01) |
| *C21N 15/09* | (2006.01) |
| *C12P 21/06* | (2006.01) |
| *C07H 21/04* | (2006.01) |

(52) U.S. Cl. ...................... 435/196; 435/69.1; 435/183; 435/193; 435/194; 435/195; 435/252.3; 435/320.1; 530/350; 536/23.2

(58) Field of Classification Search ................ 435/69.1, 435/183, 193, 194, 195, 196, 252.3, 320.1; 530/350; 536/23.2, 23.1
See application file for complete search history.

(56) References Cited

FOREIGN PATENT DOCUMENTS

WO    WO 00/58473 A2    10/2000

OTHER PUBLICATIONS

Attwood et al. Which craft is best in bioinformatics? Comput. Chem. 2001, vol. 25(4), pp. 329–339.*
Croop, "Evolutionary Relationships among ABC Transporters," *Meth. Enzym.*, 292:101–165 (1998).
Higgins, "ABC Transporters: From Microorganisms to Man," *Ann. Rev. Cell. Biol.*, 8:67–113 (1992).
Hobbs, et al., "*ABC1: connecting yellow tonsils, neuropathy, and very low HDL,*" *J. Clin. Invest.*, 104(8):1015–1017 (1999).
Klucken, et al., "AGCG1 (ABC8), the human homolog of the Drosophila white gene, is a regulator of macrophage cholesterol and phospholipid transport," PNAS, 97(2):817–822 (2000).
Lawn, et al., "The Tangier disease gene product ABC1 controls the cellular apolipoprotein–mediated lipid removal pathway," *J. Clin. Invest.*, 104(8):R25–R31 (1999).
Lee, et al., "*Identification of a gene, ABCG5, important in the regulation of dietary cholesterol absorption,*" *Nature Genetics*, 27(1):79–83 (2001).
Lee, et al., "*Identification of a gene, ABCG5, important in the regulation of dietary cholesterol absorption,*" Abstract, AC No. AF312713, Jan. 24, 2001.
Lee, et al., "*Identification of a gene, ABCG5, important in the regulation of dietary cholesterol absorption,*" Abstract, AC No. AF312715, Jan. 24, 2001.
Lehmann, et al., "Activation of the Nuclear Receptor LXR by Oxysterols Defines a New Hormone Response Pathway," *J. Biol. Chem.*, 272(6):3137–3140 (1997).
Marra, et al., "*The WashU–HHMI Mouse EST Project,*" Abstract, AC No. AA244605, Mar. 11, 1997.
Marra, et al., "*The WashU–HHMI Mouse EST Project,*" Abstract, AC No. AA239884, Mar. 6, 1997.
Patel, et al., "Mapping a Gene Involved in Regulating Dietary Cholesterol Absorption," *J. Clin. Invest.*, 102(5):1041–1044 (1998).
Sulston, et al., "*Toward a complete human genone sequence,*" Abstract, ID No. AC011242, Genome Research, 8(11):1097–1108 (1998).
Tzermia, et al., "*Sequence analysis of a 33.2 kb segment from the left arm of yeast chromosome XV reveals eight known genes and ten new open reading frames including homologues of ABC transporters, inositol phosphatases and human expressed sequence tags,*" Abstract, AC No. Q08234, Q08233, Oct. 16, 2001.
Willy, et al., "LXR, a nuclear receptor that defines a distinct retinoid response pathway," *Genes Dev.*, 9:1033–45 (1995).

* cited by examiner

*Primary Examiner*—Manjunath N. Rao
*Assistant Examiner*—Christian L. Fronda
(74) *Attorney, Agent, or Firm*—Townsend & Townsend & Crew LLP

(57) ABSTRACT

The present invention provides nucleic acids encoding a novel ABC family cholesterol transporter, SSG. The herein-disclosed sequences can be used for any of a number of purposes, including for the diagnosis and treatment of cholesterol-associated disorders, including sitosterolemia, and for the identification of molecules that associate with and/or modulate the activity of SSG.

19 Claims, 19 Drawing Sheets

LXR agonist: Cpd B, C
FXR agonist: Cpd E, F

COMPOUND C
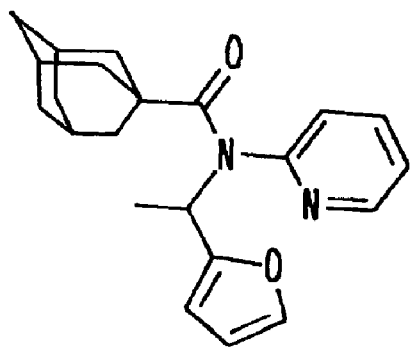
COMPOUND B
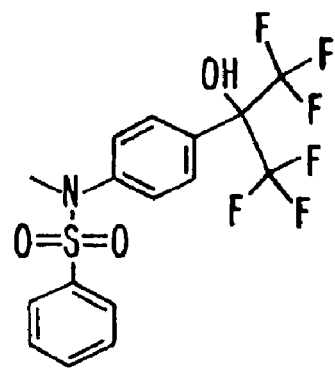
COMPOUND A
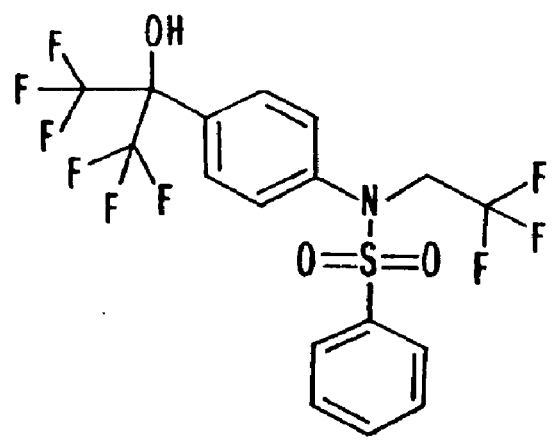
FIG. 6.

FIG. 7A.

```
GACATCTATCACAAAATTCTGGAGAACATTGAAAGAGCACGATATACCTTACCCATGTTCCTTTCAAAACAAAAGATCCTCCTGGGAT  1140
 D  I  Y  H  K  I  L  E  N  I  E  R  A  R  Y  L  K  T  L  P  M  V  P  F  K  T  K  D  P  P  G  M

GTTCGGCAAGCTTGGTGTCCTGAGGCGAGTAACAAGAACTTAATGAGGAATAAGCAGGTCAGTGATTATGCTCTCGTTCAGAATCTGATCA  1235
 F  G  K  L  G  V  L  R  R  V  T  R  N  L  M  R  N  K  Q  A  V  I  M  R  L  V  Q  N  L  I

TGGGCCTCTTCTTCTACCTTCATTTTCTACCTTCTCCGCGTCCAGAACACGCTAAAGGGCGCTGTGCAGGATCGCGTCGGCCTCTATCAGCTTGTG  1330
 M  G  L  F  I  F  Y  L  L  R  V  Q  N  N  T  L  K  G  A  V  Q  D  R  V  G  L  L  Y  Q  L  V

GGTGCCACCCCATACACCGGCATGCTCAATGCTGTTCCCATGCTGAATCTGTTTCCTATGCTCAGAGAGTCAGGATGCCTGTATCA  1425
 G  A  T  P  Y  T  G  M  L  N  A  V  N  L  F  P  M  I  R  A  V  S  D  Q  E  S  Q  D  G  L  Y  H

TAAGTGGCAGATGCTCCTGGCCTACGTGCTGCTACACGTGCTCCCCTTCAGCGTCATTTTCAGCAGTGTGTTATTGGACTCTGG  1520
 K  W  Q  M  L  L  A  Y  V  L  H  V  L  P  F  S  V  I  A  T  V  I  F  S  S  V  C  Y  W  T  L

GCTTGTATCCTGAAGTTGCCAGATTTGGATATTCTCTGCTCTTTTGGCCCCTCACTTAATTGGAGAATTTCTAACACTTGTGCTGCTTGGT  1615
 G  L  Y  P  E  V  A  R  F  G  Y  F  S  A  A  L  L  A  P  H  L  I  G  E  F  L  T  L  V  L  L  G

ATAGTCCAAAACCCTAATATTGTCAACAGTATAGTGGCTCATCTCAGCATCTCTGGGCTTCTGCTGATTATCAGAAACATACAAGA  1710
 I  V  Q  N  P  N  I  V  N  S  I  V  A  L  L  S  I  S  G  L  L  I  G  S  G  F  I  R  N  I  Q  E

AATGCCCATTCCTTTAAAAATCCTGGGTTATTTTACATTCCAAAAATACTGTTGTGAGATTCTCGTGGTCAATGAGTTTTACGGCCTGAACTTCA  1805
 M  P  I  P  L  K  I  L  G  Y  F  T  F  Q  K  Y  C  C  E  I  L  V  V  N  E  F  Y  G  L  N  F

CTTGTGTGGCAATCCAACGGCAAACTTCCTCAACACCTCTATGCTAAATCACCCGATGTGCGCCATCACCCAGGGTGTCCCAGTTCATCGAGAAAACCTGCCCAGGTGCTACA  1900
 T  C  G  S  N  T  S  M  L  N  H  P  M  C  A  I  T  Q  G  V  Q  F  I  E  K  T  C  P  G  A  T

TCCAGATTCACGGCAAACTTCCTCAATCTTATGGTTTATCCCAGCTCTGGTCATCCTAGGAATAGTGATTTTAAAGTCAGGGACTACCTGAT  1995
 S  R  F  T  A  N  F  L  I  L  Y  G  F  I  P  A  L  V  I  L  G  I  V  I  F  K  V  R  D  Y  L  I

TAGCAGATAGTTAAGATGACAGCAGGAAAGGGTTAATGGGAGCACAGCCCACTGTGCTGGAGCAGAAGTACTGTCTTCAACCATCAGGATTC  2090
 S  R  X>
```

*FIG. 7B.*

```
CATCTGCGACCCTTGTGTCTGACCCTTGTGTCTGACCCTGTGTCTGAGGGCAAGGGAGAACTCACAGCCCTCTGCTATTCCAGCTTGTGGGCAAT   2185

GTGGTGCTTGGACATTGTGACTGAACTGGTCCAATAATGTAAATAATTCATAAACCTACAGGACATT                               2258
```

FIG. 7C.

```
GTCAGGTGAGACAGGCAGTCTGCTCCCAACTGAAGCCACTCTGGGAGGGTCCGGCCACCAGAAATTTGCCCAGCTTTGCT                  95

GCCTGTTGGCCATGGGTGACCTCTCATCTTTGACCCCCGGAGGGTCTCCAAGTAAACAGAGCCTCCCAGAGCTCCCTGGAGGGGCT           190
                 M  G  D  L  S  S  L  T  P  G  G  S  M  G  L  Q  V  N  R  G  S  Q  S  L  E  G  A

CCTGCCACCGCCCCGGAGCCTCACAGCCTGGGCATCCTCCTACACAGCGTCAGCTAGCCCACCGCGTCGAGCCTGTGGACATCACATCTTG      285
 P  A  T  A  P  E  P  H  S  L  G  I  L  H  A  S  Y  S  V  S  H  R  V  R  P  W  D  I  T  S  C

CCGGCAGCAGTGGACCAGCAGATCCTCAAAGATGTCTCCTTGTACGTGGAGAGCGGGCAGATCATGTGCATCCTAGGAAGCTCAGGCTCCGGGA   380
 R  Q  W  T  R  Q  I  L  K  D  V  S  L  Y  V  E  S  G  Q  I  M  C  I  L  G  S  S  G  S  G

AAACCACGCTGCTGGACGCCATGTCCGGGAGGCTGGGCCGGGCTGGGGGAGGTGTATGTGAACGGCCGGGCTGCGCGGGAG                475
 K  T  T  L  L  D  A  M  S  G  R  L  G  R  A  G  T  F  L  G  E  V  Y  V  N  G  R  A  L  R  R  E

CAGTTCCAGGACTGCTTCTCCTACGTCCTGCAGAGCGACACCCTGCTGAGCAGCCTGACTGTCCGAGAGACGCTGCACTACACCGCGCTGCTGGC   570
 Q  F  Q  D  C  F  S  Y  V  L  Q  S  D  T  L  L  S  S  L  T  V  R  E  T  L  H  Y  T  A  L  L  A

CATCCGCCGGGCAATCCCGGCTCCTTCCGGCAGAAGAAGGTGGAGGCCGTCATGGCAGAGCTGAGCTTGAGCCATGTGGCAGACCGACTGATTGGCA   665
 I  R  G  N  P  G  S  F  Q  K  K  V  E  A  V  M  A  E  L  S  L  S  H  V  A  D  R  L  I  G

ACTACAGCTTGGGGGGCATTTCCACGGGTGAGCGCCGCCGAGTCAGCATCGCAGCCCAGCTGCTCCAGGATCCTAAGGTCATGCTGTTTGATGAG   760
 N  Y  S  L  G  G  I  S  T  G  E  R  R  V  S  I  A  A  Q  L  L  Q  D  P  K  V  M  L  F  D  E

CCAACCACAGGCCTGGACTGCATGACTGCTAATCAGATTGTCGTCCTCGTTGGTTGGTTCTCACCATTCA                           855
 P  T  B  L  D  C  M  T  A  N  Q  I  V  V  L  V  L  V  L  V  L  T  I  H
```

FIG. 8A.

```
CCAGCCCCGTTCTGAGCTTTTTCAGCTCTTTGACAAAATTGCCATCCTGAGCTTCGGAGAGCTGATTTTCTGTGGCACGCCAGCGGAAATGCTTG    950
 Q  P  R  S  E  L  F  Q  L  F  D  K  I  A  I  L  S  F  G  E  L  I  F  C  G  T  P  A  E  M  L

ATTTCTTCAATGACTGCGGTTACCCCTGTTGCCCTGAACATTCAAACCCTTTTGACTTCTATATGGACCTCAGTGGATACCCAAAGCAAGGAA    1045
 D  F  F  N  D  C  G  Y  P  C  P  E  H  S  N  P  F  D  F  Y  M  D  L  T  S  V  D  T  Q  S  K  E

CGGGAAATAGAAACCTCCAAGAGAGTCCAGATGATAGAATCAGCAATTTGTCATAAAACTTTGAAGAATATTGAAAGAAT               1140
 R  E  I  E  T  S  K  R  V  Q  M  I  E  S  A  Y  K  K  S  A  I  C  H  K  T  L  K  N  I  E  R  M

GAAACACCTGAAAACGTTACCAATGGTTCCCTTTCAAAACCAAGATTCTCCTTCTAAACTGGGTGTTCTCCTGAGGAGAGTGACAA          1235
 K  H  L  K  T  L  P  M  V  P  F  K  T  K  D  S  P  G  V  F  S  K  L  G  V  L  L  R  R  V  T

GAAACTTGGTGAGAAATAAGCTGGCAGTGATTACGCGTCTCCTTCAGAATCTGATCATGGGTTTGTTCCTCTTTTCTTCGTTCTGCGGGTCCGA   1330
 R  N  L  V  R  N  K  L  A  V  I  T  R  L  L  Q  N  L  I  M  G  L  F  L  L  F  F  V  L  R  V  R

AGCAATGTGCTAAAGGGTGCTATCCAGGACCGCGTAGGTCTCCTCCTTTACCAGTTTGTGGGCGCCACCCCGTACACAGGCATGCTGAACGCTGTGAA   1425
 S  N  V  L  K  G  A  I  Q  D  R  V  G  L  L  Y  Q  F  V  Q  A  T  P  Y  T  G  M  L  N  A  V  N

TCTGTTTCCCGTGCTGCGAGCTGTGTCAGCAGACCAGGAGAGTCAGGATGGCCTCTACTGGATGATGCTGGCCTATGCACTGCACGTCC        1520
 L  F  P  V  L  R  A  V  S  D  Q  E  S  Q  D  G  L  Y  Q  K  W  Q  M  M  L  A  Y  A  L  H  V

TCCCCTTCAGCGTTGTTGCCACCATGATTTTCAGCAGTGTGTGCTACTGGACGCTGGGCCTTACATCCTGAGGTTGCCCGATTTGGATATTTTCT   1615
 L  P  F  S  V  V  A  T  M  I  F  S  S  V  C  Y  W  T  L  G  L  H  P  E  V  A  R  F  G  Y  F  S

GCTGCTCTCTTGGCCCCCACTTAATTGGTGAATTTCTAACTCTTGTGCTACTTGTCCTCAAAATCCAAATATAGTCAACAGTGTAGTGGC       1710
 A  A  L  L  A  P  H  L  I  G  E  F  L  T  L  V  L  L  G  I  V  Q  N  P  N  I  V  N  S  V  V  A

TCTGCTGTCCATTGCGGGGGTGCTGTTGTTGGAGTCTTACGGACTGAATTTCACTTGTGGCAGCTCAAATGTTTCTGTGACAACTAATCCA      1805
 L  L  S  I  A  G  V  L  V  G  S  G  F  L  R  N  I  Q  E  M  P  I  P  F  K  I  I  S  Y  F  T

TCCAAAAAATATTGCAGTGAGATTCTTGTAGTCAATGAGTTCTACGGACTGAATTTCACTTGTGGCAGCTCAAATGTTTCTGTGACAACTAATCCA   1900
 F  Q  K  Y  C  S  E  I  L  V  V  N  E  F  Y  G  L  N  F  T  C  G  S  S  N  V  S  V  T  T  N  P
```

*FIG. 8B.*

```
ATGTGTGCCTTCACTCAAGGAATTCAATTCATTGAGAAAAACCTGCCCAGGTGCAACATCTAGATTCACAATGAACTTTCTGATTTTGTATTCATT  1995
 M  C  A  F  T  Q  G  I  Q  F  I  E  K  T  C  P  G  A  T  S  R  F  T  M  N  F  L  I  L  Y  S  F

TATTCCAGCTCTCTTGTCATCCTAGGAATAGTTGTTTTCAAATAAGGATCATCTCATTAGCAGTAGTGAAAGCCATGGCTGGGAAAATGGAAGT  2090
 I  P  A  L  V  I  L  G  I  V  V  F  K  I  R  D  H  L  I  S  R  X>

GAAGCTGCCGACTGTGCATGACTGTCTGAACGTCTCTGAAATGAGAGTGCCATGTATTCTTTTCTTGACAGGACATCTCAAGTCTTTTAACCATTA  2185

AGACTCCATTTGTGCCTCTCTTGGATCCAAGCAGCCTTGAATGCAATGAAGTGGTTTATAGTCCCCTTGCTCTTACAACTTGCAGGGACATGTGGT  2280

TATTTGAAATTGTGACTGAGCGGACCCAAGAATGTAAATAATGTAAATATTCATAAACCTATGGG  2340
```

FIG. 8C.

```
hSSG.pro  MGDISSITPG GSMGLQVNRG SQSSLEGAPA TAPEP-HSLG ILHASYSVSH RVRPWWDITS CRQQMTRQIL KDVSLYVESG   79
mSSG.pro  MGELPLSPE  GARGPHINRG SISSLEQGSV TGTEARHSLG VLHMSYSVSN RVGPWWNIKS COQKMDRQIL KDVSLYHESG   80 hSSG.pro  QIMCILGSSG SGKTTLLDAM SGRIGRAGTF LGEVYWNGRA LRREQFQDCF SYVLQSDTLL SSLTVRETIH YTALLAIRRG  159
mSSG.pro  QIMCILGSSG SGKTTLLDAI SGRIRRIGTL EGEVFVNGCE LRRDQFQDCF SYVLQSDVFL SSLTVRETIR YTAMLALCRS  160 hSSG.pro  NPGSFQKKVE AVMAELSLSH VADRLIGNYS IGGISTGERR RVSIAAQLLQ DPKVMLFDEP TTGLDCMTAN QIVMIVELA   239
mSSG.pro  SADFYNKKVE AVMTELSLSH VADQMGSYN  EGGISSGERR RVSIAAQLLQ DPKVMMIDEP TTGLDCMTAN QIVLIAELA   240 hSSG.pro  RRNRIVLTI  HQPRSELFQL FDKIAILSFG EIIFCGTPAE MIDFFNDCGY PCPEHSNPFD FYMDLTSVDT QSKERETETS  319
mSSG.pro  RRDRIVIVTI HQPRSELFQH FDKIAILTYG EIVFCGTBEE MIGEFNNCGY PCPEHSNPFD FYMDLTSVDT QSRERETETY  320 hSSG.pro  KRVQMIESAY RKSAICHKIL KNIERMKHLK TLPMVPFKTK DSPGVFSKLG VLLRRVTRNL VRNKLAVIIR LQNLIMGLF   399
mSSG.pro  KRVQMLECAF KEISDIYHKIL ENIERARYLK TLPMVPFKTK DPPGMEGKLG VLLRRVTRNL MRNKQAVIMR LVQNLIMGLF   400 hSSG.pro  LFFVLRVRS  NVLKGAHQDR VGLLYQFVGA TPYTGMLNAV NLFPVLRAVS DQESQDGLYQ KWQMLAYAL HVLPFSVMAT  479
mSSG.pro  LFYLLRVQN  NTLKGAMQDR VGLLYQIVGA TPYTGMLNAV NLFMLRAVS DQESQDGLYH KWQMLAYML HVLPFSVMAT  480 hSSG.pro  MFSSVCYWT  LGLHPEVARF GYFSAALLAP HLIGEFLTIV LLGIVQNPNI VNSMVALLSI AGMVGSGFL RNIQEMPIPF  559
mSSG.pro  VLFSSVCYWT LGLMPEVARF GYFSAALLAP HLIGEFLTIV LLGIVQNPNI VNSIVALLSI SGILIGSGFI RNIQEMPIPL  560 hSSG.pro  KIISYFTFQK YCSEILVVNE FYGLNFTCGS SMSVTNPM CATTQGIQFI EKTCPGATSR FTMNFLILYS FIPALVILGI  639
mSSG.pro  KILGYFTFQK YCCEILVVNE FYGLNFTCGG SNISMLNHPM CAITQGMQFI EKTCPGATSR FTANFLILYG FIPALVILGI  640 hSSG.pro  VMFKIRDHLI SR  651
mSSG.pro  VIEKVRDYLI SR  652
```

FIG. 9.

Reference Number: 6711
Stanford RH Panel: TNG4
Lowest LDD Reported: 5
Chromosome Value: 0

Results for HT

Submitted
Vector:000100000000100010000101001000000100000010001000
00000000100000000000100000000001000100

SHGCNAME CHROM# LOD_SCORE DIST.(cRs)

1 SHGC-36672 2 7.52 35
Vector:00000000R0000101010010001001110000010000010001000
0000001010000000000010000000000R01000100

2 SHGC-8189 2 6.53 44
Vector:000000001000010101001000100111000001000000100010000
00000101000000000001000000000101000100

3 SHGC-699 2 6.03 48
Vector:000100000000100010000101001010010000100011000100010000
1000001010000000000000001000000011000100

The number of markers searched was 32440

FIG. 10.

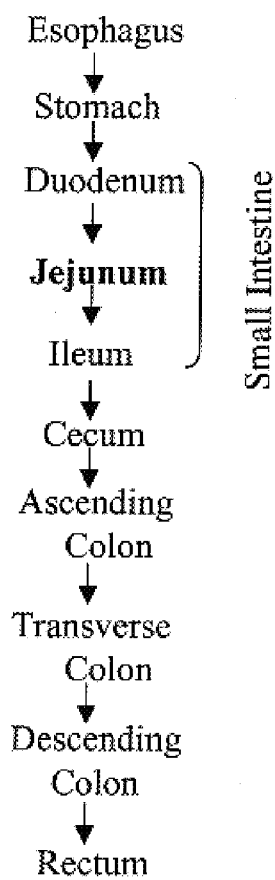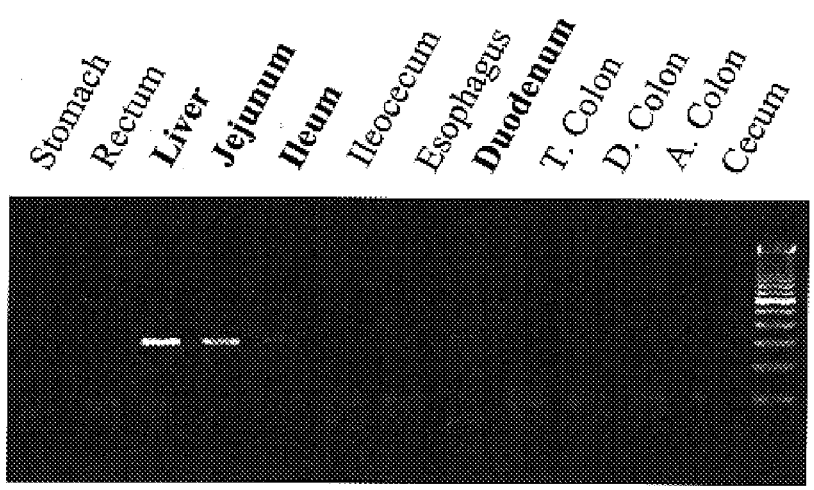
FIG. 11.

```
GTCAGGTGGAGCAGGCAGGCAGTCTGCCACGGGCTCCCCAACTGAAGCCACTCTGGGGAGGTCCGGCCACCAGAAAATTTGCCCAGCTTTGCTGCCT
                                                        |----EXON 1------------------------------|

TGTGGCCATGGGTGACCTCTCATCTTTGACCCCGGAGGGTCTCCAAGTAAACAGAGGCTCCCAGAGCTCCCTGGAGGGCTCCTGCCAC
                                                                                |----EXON 1----|

CGCCCCGGAGCCTCACAGCCTGGGCATCCTCCATGCCTCTACAGCGTCAG|CCACCGGCGTGAGGCCCTGAGGCCCGTGGGACATCACATCTTGCCGGCAGCAGTG
|----EXON 1--------------------------------------|                                |----EXON 2-----|

GACCAGGCAGATCCTCAAAGATGTCTCCTTGTACGTGGAGAGCGGGCAGATCATGTGCATCCTAGGAAGCTCAG|CGCCCGGGAAAACCACGCTGCTGGA
                             |----EXON 2-----------------------------|                   |---EXON 3---|

CGCCATGTCCGGGAGCTGGGGCGCGGGGACCTTCCTGGGGAGCGTGTATGTGAACGGCCGGGCTGCGCGAGACGCTGCACTACACCGCGTGCTGCGGCAATCCCGGCTC
|----EXON 3---------------------------------------------------------------|

CTACGTCCTGCAG|AGCGACACCCCTGCTGAGCAGCCTGAGCCGTGCGCGTGCTGCCATCCGCCCGGCGCAATCCCGGCTC
|--EXON 3-|                                                                  |

CTTCCAGAAGAAGGTGG|AGGCCGTCATGGCCAGAGCTGAGTCTCTGAGCCATGTGGCAACTACAGCTTGGGGGCATTTCCACGGG
|----EXON 4--|                    |----EXON 5-----------------------------------|

TGAGCGGCGCCGGGTCTCCATCGCAGCCAGCTGCTCCAGGATCCTA|AGGTCATGCTGTTTGATGAGCCAACCACAGGCCTGACTGCATGACTGCTAA
|----EXON 5------------------------------|                |----EXON 6---------------------------|

TCAGATTGTCGTCCTGGTGAGCTGCTCGCAGGAACCCGAATTGTGGTTCTCACCATTCACCAGCCCCGTTTCTGAGCTTTTTCAG|CTCTTTGACA
                                             |----EXON 6--------------------------|            |EXON 7|

AAATTGCCATCCTGAGCTTCGGAGAGCTGATTTTCTGTGGCACGCAGCGGAAATGCTTGATTTCTTCAATGACTGGGTTACCCTTGTCCTGAACATT
                                                                         |----EXON 7------------|

CAAACCCTTTGACTTCTATA|TGGACCTGCAGTGGATACCCAAAGCAAGAAATAGAAACCTCCAAGAGAGTCCAGATGATAGAATCTG
|----EXON 7-------|                                    |----EXON 8----|
```

*FIG. 14B. (1 OF 3)*

```
CCTACAAGAGAAATCAGCAATTTGTCATAAAACTTTGAAGAATATTGAAGAATATTGAAAACACCTGAAAACGTTACCAATGGTTCCTTTCAAAACCAAAGATT
----EXON 8----

CTCCTGGAGTTTTCTCTAAACTGGGTGTTCTCCTGAGGAGAGTGACAAGAAACTTGGTGAGAATAAGCTGGCAGTGATTACGCGTCCTTCAGAATC
----EXON 8---- ----EXON 9----

TGATCATGGGTTTGTTCCTCCTTTTCTCGTTCTGCGGGTCCGAAGCAATGTGCTAAAGGGTGCTATCCAGGACCGCGTAGTGTCTCCTTTACCAGTTTG
----EXON 9----

TGGGCGCCACCCCGTACACAGGCATGCTGAACGCTGTGAATCTGTTTCCCGTGCTGCGAGCTGTCAGCGACCAGGAGAGTCAGGACGGCCTCTACCAGA
----EXON 9---- ----EXON 10----

AGTGGCAGATGATGCTGGCCTATGCACTGCCACGTCCTCCCCTTCAGCGTTGTTGCCACCATGATTTTCAGCAGTGTGCTACTGGACGCTGGCTTAC
----EXON 10---- ----EXON 11----

ATCCAAATATAGTCAACAGTGTCTGCTTGGCTCCATTGCGGGGGTGCTTGTTGGATCTCGATTCCTCAGAAACATACAAGAAAATGCCCATTCCTT
----EXON 11---- ----EXON 12----

TTAAAATCATCAGTTATTTTACATTCCAAAAATATATTGCAGTGAGATTCTTGTAGTCAATGAGTTCTACGGACTGAATTCACTTGTGGCAGTCAAATG
----EXON 12---- ----EXON 13----

TTTCTGTGACAACTAATCCAATGTGTGCCTTCACTCAAGGAATTCAATTCATTGAGAAAACCTGCCCAGTGCAACATCTAGATTCACAATGAACTTTC
----EXON 13----

TGATTTTGTATTCATTTATTCCAGCTCTTGTCATCCTAGGAATAGTTGTTTTCAAAATAAGGGATCATCTCATTAGCAGGTAGTGAAAGCCATGGCTGG
----EXON 13----

GAAAATGGAAGTGAAGCTGCCGACTGTGCATGACTGCTCTGAACGTCTGAAATGAGAGTGCCATGTATTTCTTTCTTGACAGGACATCTCAAGTCTTTT
----EXON 13----
```

FIG. 14B. (2 OF 3)

AACCATTAAGACTCCATTTGTGCCTCTTGGATCCAAGCAGGCCTTGAATGCAATGGAAGTGGTTTATAGTCCCCTGCTCTTACAACTTGCAGGGACATG
-----------------------------------------EXON 13----------------------------------------------

TGGTTATTTGGAAATTGTGACTGAGCGGACCCAAGAATGTAAATAATATTCATAAACCTATGGG
---------EXON 13----------

| EXON NUMBER | EXON SIZE | 5' SPLICING SITE | 3' SPLICING SITE | INTRON SIZE |
|---|---|---|---|---|
| 1 | 124 | cctttaaagCCACCGC | GCGTCAGgtaaggcag | ~600bp |
| 2 | 137 | gccccgcagGCTCCGG | AGCTCAGgtaagcttg | ~6kb |
| 3 | 103 | ctcctgcagAGCGACA | CCTGCAGgtgggcgcg | 74bp |
| 4 | 129 | tgcaggtggAGGCCGT | AAGGTGGgtgcagccc | ~4kb |
| 5 | 140 | tgctggcagAGGTCAT | GATCCTAgtaagtggc | ~2kb |
| 6 | 130 | tctggtcagCTCTTTG | TTTTCAGgtaagaggt | ~2.5kb |
| 7 | 214 | aactttagTGGACCT | TTCTATAgtaagtttt | ~0.5kb |
| 8 | 206 | tgttttcagGAGAGTG | TCCTGAGgtaagaggc | 100bp |
| 9 | 139 | catcccagTTCCCGT | AATCTGTgtaagtgcc | ~1.7kb |
| 10 | 186 | cttttctagGACGCTG | GCTACTGgtgagggtt | ~1.9kb |
| 11 | 113 | tttcttaagAAACATA | TCCTCAGgtaagatat | ~5.3kb |
| 12 |  | ccttgacagGCAGCTC | ACTTGTGgtaagtatt | ~1.2kb |
| 13 |  |  |  |  |
| TOTAL |  |  |  | ~25.9kb |

EXONIC SEQUENCES IN CAPITAL LETTER

FIG. 14B.(3 OF 3)

SITOSTEROLEMIA SUSCEPTIBILITY GENE (SSG): COMPOSITIONS AND METHODS OF USE

CROSS-REFERENCES TO RELATED APPLICATIONS

This application claims benefit of U.S. Provisional Application Nos. 60/198,465, filed Apr. 18, 2000, and 60/204,234, filed May 15, 2000, which applications are incorporated herein by reference for all purposes.

BACKGROUND OF THE INVENTION

Cholesterol is a soft, waxy substance that is present in the bloodstream and in all cells. It is used to help digest fats, to help form cell membranes, and is an important precursor of many hormones. Although cholesterol plays an essential role in many key processes in the body, too much cholesterol in the blood (called hypercholesterolemia) can be dangerous: high cholesterol levels can lead, e.g., to the accumulation of cholesterol on artery walls, thereby elevating the risk of a number of cardiovascular disorders, including blood clots, heart attacks and stroke. In addition, one factor in the development of atherosclerosis is the formation of foam cells, i.e., macrophages or smooth muscle cells that contain high amounts of lipids such as cholesterol.

In animals, cholesterol is obtained from both external and internal sources. All animals can synthesize cholesterol de novo, which occurs mostly in the liver. In addition, a large amount of cholesterol is obtained from animal-based sources of food.

An important cause of hypercholesterolemia in humans is the absorption of excess cholesterol in the diet. While some cholesterol can be removed from the body, through the liver, this removal is often insufficient to lower cholesterol levels in patients with hypercholesterolemia to safe levels.

Sitosterolemia is a rare, recessive, inherited lipid disorder characterized by a multitude of symptoms, including xanthomas, atherosclerosis, elevated sitosterol levels, myocardial infarction, arthritis, and chronic hemolytic anemia. Sitosterolemia has been associated with an increased absorption, and decreased elimination, of dietary cholesterol as well as plant sterols, such as sitosterol, which are normally not absorbed from the diet (see, e.g., Online Mendelian Inheritance in Man (OMIM) entry 210250). The gene underlying sitosterolemia has been mapped to genomic region 2p21 (Patel et al., *J. Clin. Invest.* 102:1041–1044 (1998)).

The ATP binding cassette (ABC) family of transporters represents a large number of evolutionarily related transmembrane proteins that are involved in the transport of a diversity of substrates, including ions, drugs, peptides, and lipids, and which have been found in a large number of prokaryotic and eukaryotic organisms (for review, see, Higgins, *Ann. Rev. Cell. Biol.* 8:67–113 (1992); Croop, *Meth. Enzym.* 292:101–165 (1998); see, also, http://www.med.rug.nl/mdl/humanabc.htm for a list of human ATP family members).

Certain ABC family members have been associated with the transport of cholesterol and other lipids. ABC1, which has been shown to transport cholesterol and other lipids, has been linked to Tangier disease (see, e.g., Hobbs et al., *J. Clin. Invest.* 104:1015–1017 (1999); Lawn et al., *J. Clin. Invest.* 104:R25–R31 (1999)). In addition, ABC8, also referred to as ABCG1, has been shown to be involved in the transport of cholesterol and other lipids. While ABC1 is known to act as a monomer, ABC8 is a "half site" family member, which are thought to require dimerization to function as a transporter.

Recently, liver X receptors (LXRs) have been identified as key components in cholesterol homeostasis. Two LXR proteins ($\alpha$ and $\beta$) are known to exist in mammals. The expression of LXR$\alpha$ is restricted, with the highest levels being found in the liver, and lower levels found in kidney, intestine, spleen, and adrenals (see Willy, et al, *Genes Dev.* 9(9):1033–45 (1995)). LXR$\beta$ is rather ubiquitous, being found in nearly all tissues examined. Recent studies on the LXRs indicate that they are activated by certain naturally occurring, oxidized derivatives of cholesterol, including 22(R)-hydroxycholesterol, 24(S)-hydroxycholesterol and 24,25(S)-epoxycholesterol (see Lehmann, et al., *J. Biol. Chem.* 272(6):3137–3140 (1997)).

Mice lacking the receptor LXR$\alpha$ (e.g., knockout or (–/–) mice) lose their ability to respond normally to increases in dietary cholesterol and are unable to tolerate any cholesterol in excess of that synthesized de novo. These results have established the essential role of LXR$\alpha$ in the regulation of cholesterol homeostasis.

Clearly, new approaches for reducing the absorption of dietary cholesterol, for maximizing the elimination of excess cholesterol from the liver, and for preventing the development of foam cells would have tremendous public health benefits. The present invention addresses these and other needs.

SUMMARY OF THE INVENTION

The present invention provides nucleic acids encoding a novel ABC family sterol transporter, called the Sitosterolemia Susceptibility Gene, or SSG. The herein-disclosed sequences can be used for any of a number of purposes, including for the diagnosis and treatment of sterol-associated disorders, including sitosterolemia, and for the identification of molecules that associate with and/or modulate the activity of SSG.

In one aspect, the present invention provides an isolated nucleic acid encoding an SSG polypeptide, the polypeptide comprising at least about 70% amino acid sequence identity to an amino acid sequence as set forth in SEQ ID NO:1 or 3.

In one embodiment, the polypeptide specifically binds to polyclonal antibodies generated against a polypeptide that comprises an amino acid sequence of SEQ ID NO:1, 3, 5 or 6. In another embodiment, the polypeptide comprises an amino acid sequence of SEQ ID NO:1, 3, 5, or 6. In another embodiment, the polypeptide forms a dimer with a second ABC polypeptide, wherein the dimer comprises sterol transport activity. In another embodiment, the dimer is a heterodimer. In another embodiment, the sterol is cholesterol. In another embodiment, the second ABC polypeptide is ABC8. In another embodiment, the nucleic acid hybridizes under moderately stringent hybridization conditions to a nucleic acid comprising a nucleotide sequence of SEQ ID NO:2 or 4. In another embodiment, the nucleic acid hybridizes under stringent hybridization conditions to a nucleic acid comprising a nucleotide sequence of SEQ ID NO:2 or 4. In another embodiment, the nucleic acid comprises a nucleotide sequence that is at least about 70% identical to SEQ ID NO:2 or 4. In another embodiment, the nucleic acid comprises a nucleotide sequence of SEQ ID NO:2 or 4. In another embodiment, the nucleic acid is greater than 502, 1000, 1500, 2000, or more nucleotides in length. In another embodiment, the nucleic acid is from a mouse or a human.

In another embodiment, the nucleic acid is expressed in the intestine or the liver in the presence of an LXR agonist. In another embodiment, the nucleic acid is expressed in the liver, the jejunum, the ileum, or the duodenum.

In another aspect, the present invention provides a nucleic acid encoding an SSG polypeptide, the polypeptide comprising an amino acid sequence as set forth in SEQ ID NO:5 or SEQ ID NO:6.

In another aspect, the present invention provides an expression cassette comprising any of the above-described nucleic acids. In another aspect, the present invention provides an isolated cell comprising the expression cassette.

In another embodiment, the present invention provides an isolated nucleic acid comprising at least one nucleotide sequence selected from the group consisting of exon 1 (SEQ ID NO:7), exon 2 (SEQ ID NO:8), exon 3 (SEQ ID NO:9), exon 4 (SEQ ID NO:10), exon 5 (SEQ ID NO:11), exon 6 (SEQ ID NO:12), exon 7 (SEQ ID NO:13), exon 8 (SEQ ID NO:14), exon 9 (SEQ ID NO:15), exon 10 (SEQ ID NO:16), exon 11 (SEQ ID NO:17), exon 12 (SEQ ID NO:18) and exon 13 (SEQ ID NO:19). In a presently preferred embodiment, the nucleic acid comprises more than one exon. In another presently preferred embodiment, the nucleic acid further comprises at least one intron.

In another aspect, the present invention provides an isolated SSG polypeptide, the polypeptide comprising an amino acid sequence that is at least about 70% identical to SEQ ID NO:1 or 3.

In one embodiment, the polypeptide selectively binds to polyclonal antibodies generated against a polypeptide comprising an amino acid sequence of SEQ ID NO:1 or 3. In another embodiment, the polypeptide comprises an amino acid sequence of SEQ ID NO:1 or 3. In another embodiment, the polypeptide forms a dimer with a second ABC polypeptide, wherein the dimer comprises sterol transport activity. In another embodiment, the dimer is a heterodimer. In another embodiment, the second ABC polypeptide is ABC8. In another embodiment, the sterol is cholesterol. In another embodiment, the polypeptide is expressed in the intestine or the liver in the presence of an LXR agonist. In another embodiment, the polypeptide is expressed in the liver, jejunum, ileum, or duodenum. In another embodiment, the polypeptide is from a mouse or a human.

In another aspect, the present invention provides antibodies generated against a polypeptide comprising an amino acid sequence having at least about 70% amino acid sequence identity to SEQ ID NO:1 or 3.

In another aspect, the present invention provides an isolated SSG polypeptide comprising an amino acid sequence of SEQ ID NO:5 or SEQ ID NO:6.

In another aspect, the present invention provides a method of making an SSG polypeptide, the method comprising (i) introducing a nucleic acid encoding an SSG polypeptide comprising an amino acid sequence having at least about 70% amino acid sequence identity to SEQ ID NO:1 or 3 into a host cell or cellular extract; (ii) incubating the host cell or cellular extract under conditions such that the SSG polypeptide is expressed in the host cell or cellular extract.

In one embodiment, the method further comprises recovering the SSG polypeptide from the host cell or cellular extract.

In another aspect, the present invention provides a method of identifying a compound useful in the treatment or prevention of a sterol-related disorder, the method comprising contacting an SSG polypeptide with a test agent, and determining the functional effect of the test agent upon the polypeptide, wherein a functional effect exerted on the polypeptide by the test agent indicates that the test agent is a compound useful in the treatment or prevention of the sterol-related disorder.

In one embodiment, the sterol is cholesterol. In another embodiment, the polypeptide comprises an amino acid sequence that is at least about 70% amino acid sequence identical to an amino acid sequence of SEQ ID NO:1 or 3. In another embodiment, the polypeptide is present in a cell or cell membrane. In another embodiment, the polypeptide is bound to a heterologous ABC polypeptide, forming a heterodimer. In another embodiment, the functional effect comprises an increase in the sterol transport activity of the polypeptide. In another embodiment, the functional effect comprises a physical interaction between the test agent and the polypeptide. In another embodiment, the physical interaction is detected using a direct binding assay. In another embodiment, the sterol-related disorder is sitosterolemia. In another embodiment, the sterol-related disorder is selected from the group consisting of hypercholesterolemia, hyperlipidemia, gall stones, HDL deficiency, atherosclerosis, and nutritional deficiencies.

In another aspect, the present invention provides a method of identifying a compound useful in the treatment or prevention of a sterol-related disorder, the method comprising contacting a cell with a test agent and determining the functional effect of the test agent upon the cell, wherein the cell expresses or is capable of expressing an SSG polypeptide, and wherein a functional effect exerted on the cell by the test agent indicates that the test agent is a compound useful in the treatment or prevention of the sterol-related disorder.

In one embodiment, the sterol is cholesterol. In another embodiment, the polypeptide comprises an amino acid sequence that is at least about 70% amino acid sequence identical to an amino acid sequence of SEQ ID NO:1 or 3. In another embodiment, the compound produces an increase in the expression of an SSG gene that encodes the polypeptide. In another embodiment, the increase in the expression of the SSG gene is detected by detecting the level of SSG mRNA in the cell. In another embodiment, the increase in the expression of the SSG gene is detected by detecting the level of SSG polypeptide in the cell. In another embodiment, the increase in the expression of the SSG gene is detected by detecting the level of SSG protein activity in the cell. In another embodiment, the compound modulates the level of sterol transport activity in the cell. In another embodiment, the sterol transport activity is detected by detecting the rate of sterol efflux in the cell. In another embodiment, the increase in the level of expression of the SSG gene is mediated by LXR or RXR. In another embodiment, the sterol-related disorder is sitosterolemia. In another embodiment, the sterol-related disorder is selected from the group consisting of hypercholesterolemia, hyperlipidemia, gall stones, HDL deficiency, atherosclerosis, and nutritional deficiencies.

In another aspect, the present invention provides a method of treating or preventing a sterol-related disorder in a mammal, the method comprising administering to the mammal a compound that increases the level of expression or activity of an SSG polypeptide in a plurality of cells of the mammal.

In one embodiment, the sterol is cholesterol. In another embodiment, the cholesterol-related disorder is sitosterolemia. In another embodiment, the sterol-related disorder is selected from the group consisting of hypercholesterolemia, hyperlipidemia, gall stones, HDL deficiency, atherosclerosis, and nutritional deficiencies. In another embodiment, the compound produces a decrease in the amount of dietary sterol that is absorbed in the mammal. In another embodiment, the compound produces a decrease in the amount of sterol that is retained in the liver of the mammal. In another embodiment, the compound inhibits the development of foam cells within the mammal. In another embodiment, the compound causes an increase in LXR or RXR activity in the mammal. In another embodiment, the compound is identified by contacting an SSG polypeptide with a test agent and determining the functional effect of the test agent upon the polypeptide, wherein a functional effect exerted on the polypeptide by the test agent indicates that the test agent is a compound useful in the treatment or prevention of the sterol-related disorder. In another embodiment, the compound is identified by contacting a cell with a test agent and determining the functional effect of the test agent upon the cell, wherein the cell expresses or is capable of expressing an SSG polypeptide, and wherein a functional effect exerted on the cell by the test agent indicates that the test agent is a compound useful in the treatment or prevention of the sterol-related disorder.

In another aspect, the present invention provides a method of prescreening to identify a candidate therapeutic agent that modulates SSG activity in a mammal, the method comprising (i) providing a cell which comprises an SSG polypeptide; (ii) providing a test compound; and (3) determining whether the amount of sterol transport activity in the cell is increased or decreased in the presence of the test compound relative to the activity in the absence of the test compound; wherein a test compound that causes an increase or decrease in the amount of sterol transport activity is a candidate therapeutic agent for modulation of SSG activity in a mammal.

In one embodiment, the method further comprises a secondary step, wherein the test compound is administered to a mammal, and the absorption of dietary sterol in the mammal is detected.

In another aspect, the present invention provides a method of inducing the expression of an ABC gene in a mammalian cell, the method comprising increasing the level of LXR or RXR activity in said cell.

In one embodiment, the ABC gene encodes a protein that is involved in the transport of a sterol. In another embodiment, the ABC gene is selected from the group consisting of SSG, ABC1 and ABC8. In another embodiment, the sterol is cholesterol. In another embodiment, the LXR or RXR activity is increased by administering an LXR or RXR agonist to said cell. In another embodiment, the cell is present in a mammal. In another embodiment, the cell is a liver, intestinal, or kidney cell.

BRIEF DESCRIPTION OF THE DRAWINGS

FIG. 6 provides the structures of the LXR agonists Compounds A, B, and C.

FIG. 7 shows the amino acid and nucleotide sequence for mouse SSG (SEQ ID NOS:1 and 2).

FIG. 8 shows the amino acid and nucleotide sequence for human SSG (SEQ ID NOS:3 and 4).

FIG. 9 shows a comparison between the mouse and human (SEQ ID NO:1) and human (SEQ ID NO:3) SSG amino acid sequences.

FIG. 10 shows the results of a mapping experiment for SSG using the Stanford human TNG Radiation Hybrid Panel (Research Genetics), confirming the map position of human SSG of between markers D2S177 and D2S119.

FIG. 11 shows the results of PCR using SSG specific primers and cDNA panels from various tissues.

DESCRIPTION OF THE SPECIFIC EMBODIMENTS

I. Introduction

Figure 14A:
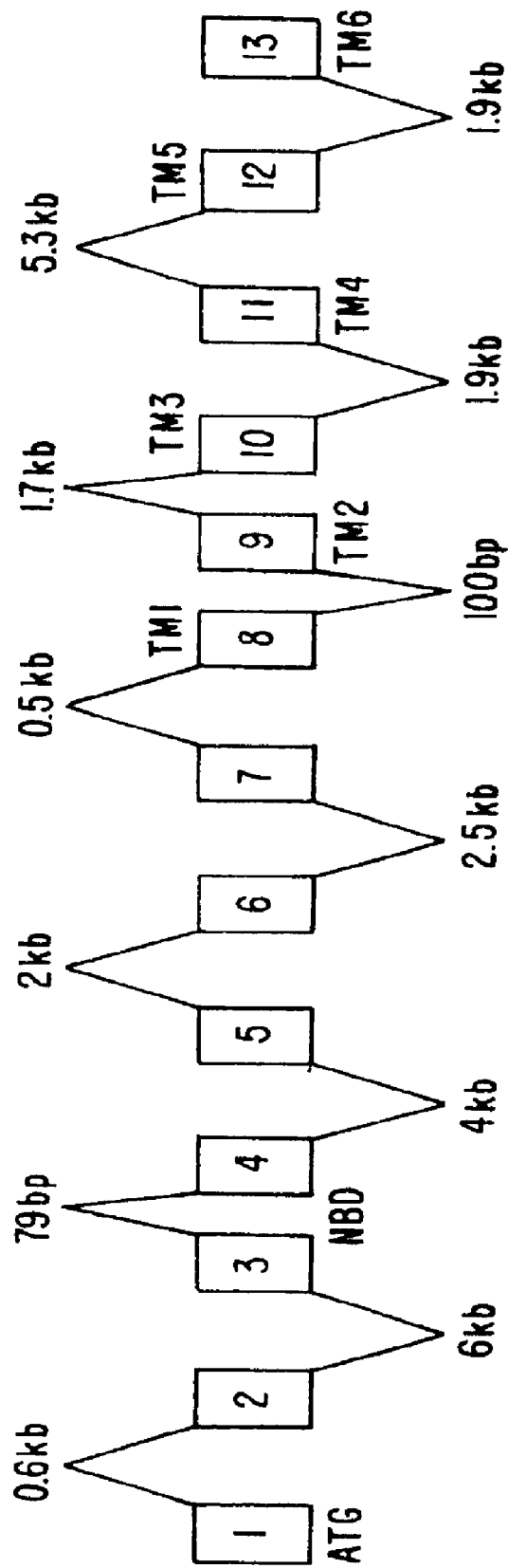
FIG. 14 illustrates the cDNA cloning and genomic organization of SSG (or ABCG5) (A). The predicted human and mouse proteins share 80% identity and are 28% identical to *Drosophilia* Brown. Human SSG (SEQ ID NO:4) contains 13 exons (SEQ ID NOS:7–19) and spans at least 25 kb of genomic DNA (B). 5' splicing sites (SEQ ID NOS:21, 23, 25, 27, 29, 31, 33, 35, 37, 39, 41 and 43) and 3' splicing sites (SEQ ID NOS:20, 22, 24, 26, 28, 30, 32, 34, 36, 38, 40 and 42) are also shown.

The present invention provides nucleic acids and polypeptides for SSG, a novel member of the ABC family of transporter molecules. Members of the ATP-binding cassette (ABC) family use ATP to drive the transport of any of a large number of molecules across membranes. SSG is involved in the transport of cholesterol and other sterols, as well as other lipids, across membranes, and is associated with the human disorder sitosterolemia. SSG sequences from human (see, e.g., SEQ ID NOs: 3 and 4) and mouse (see, e.g., SEQ ID NOs: 1 and 2) are provided. Human SSG contains 13 exons and spans at least 25 kb of genomic DNA (see, FIGS. 14(A) and (B)). The genomic position of human (2p21) and mouse (chromosome 17) SSG is also provided. Significantly, the map position of human SSG corresponds precisely to the map position of the sitosterolemia-causing gene (see, e.g., Patel et al., *J. Clin. Invest.* 102:1041–1044 (1998)).

Without being bound by the following theories, it is speculated that SSG acts to effect sterol transport activity as a monomer or, more preferably, as a homodimer or heterodimer. In particular, it is speculated that, at least in certain cells, SSG binds to the ABC8 transporter to achieve sterol transport activity (see, e.g., Klucken et al., *PNAS* 97:817–822 (2000)) for the following reasons: (i) both SSG and ABC8 belong to the subgroup of "half size transporters," which need to bind to additional ABC members for transport activity; (ii) both SSG and ABC8 are involved in sterol transport; (iii) SSG is homologous to the *Drosophila* brown and scarlet genes, and ABC8 is homologous to the *Drosophila* white gene, and, in *Drosophila*, the proteins encoded by brown and scarlet bind to the protein encoded by white.

Figure 5:
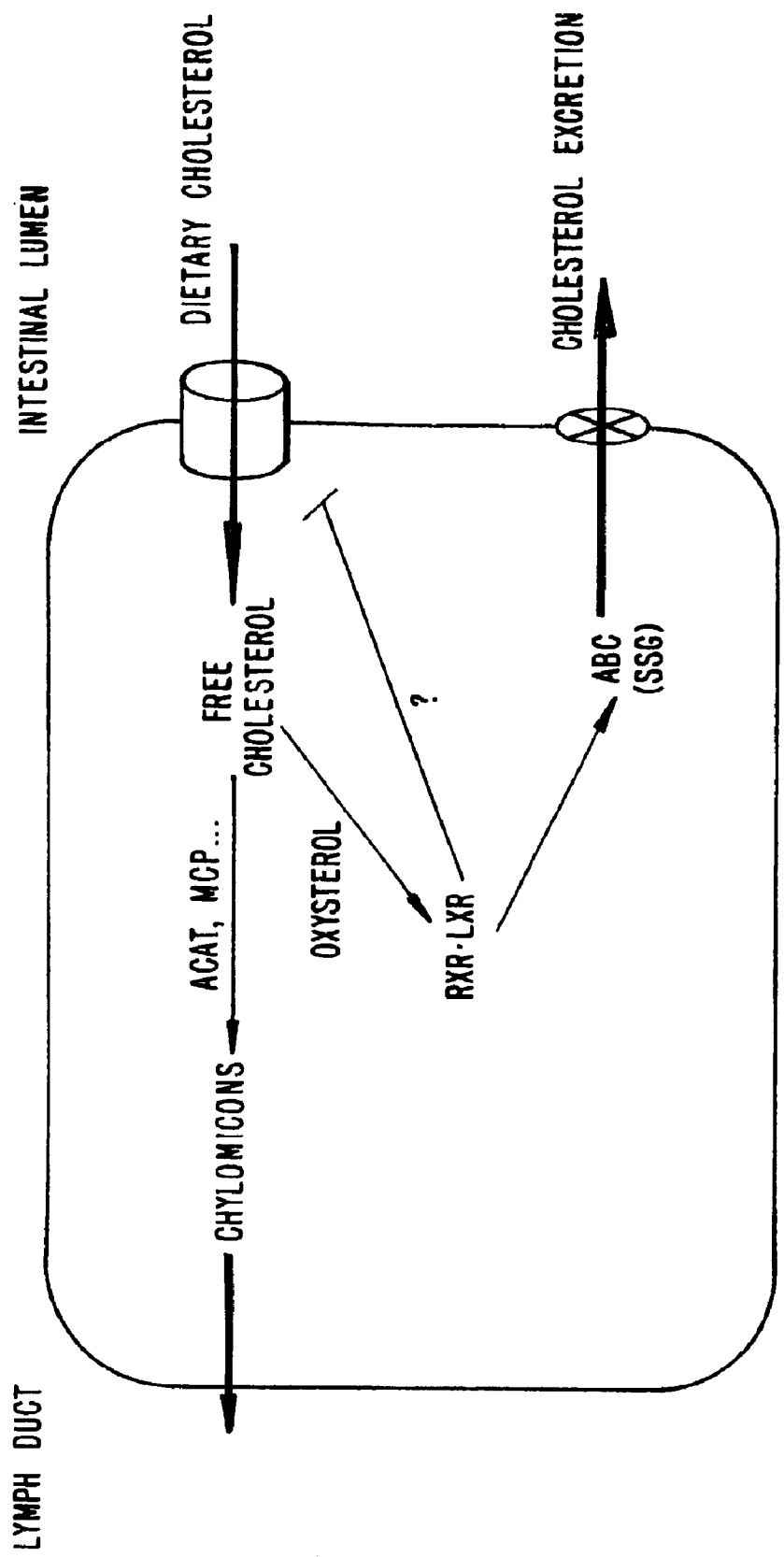
FIG. 5 provides a model for the role of SSG, and the regulation of SSG by LXR-RXR, in cells lining the intestinal lumen. According to this model, SSG plays a role in sterol efflux from the cells lining the intestinal lumen, i.e. SSG plays a role in counteracting the absorption of sterol from the intestine, thus explaining the elevated sterol levels in sitosterolemia patients who lack SSG function.

It is further speculated that, in patients with sitosterolemia, the gene encoding the SSG moiety of the SSG-ABC8 heterodimer is mutated, thereby eliminating function of the heterodimer and abolishing sterol transport activity in cells. Because the SSG-ABC8 heterodimer is speculated to cause sterol, e.g., cholesterol, efflux from cells (e.g., out of intestinal cells into the lumen, out of liver cells to allow clearance of cholesterol from the liver, and out of macrophages or smooth muscle cells to counteract foam cell formation; see, e.g., FIG. 5), a loss of transporter activity leads to an increase in the absorption of dietary cholesterol and other sterols and to an increase in foam cell formation. Accordingly, by increasing SSG activity, it is possible to lower the absorption of dietary cholesterol and other sterols and to inhibit the development of foam cells. Such benefits can be achieved in any patient, e.g., to provide a treatment for sitosterolemia, hypercholesterolemia, atherosclerosis, coronary heart disease, hyperlipidemia, HDL deficiency, cholesterol gall stones, nutritional deficiencies, etc., or to prevent the development of any of these conditions in at risk patients.

The present invention is also based on the discovery that LXR or RXR (e.g., as an LXR-RXR heterodimer) activation, e.g., by LXR or RXR agonists including synthetic and endogenous agonists, can induce the expression of ABC family members, in particular ABC family members involved in sterol transport including, but not limited to, SSG, ABC8, and ABC1. In particular, LXR or RXR activation leads to a dramatic increase in the transcription of ABC family members, as described in the Examples, infra. Accordingly, enhancing LXR or RXR activity in cells, e.g., intestinal, liver, kidney, macrophage, or smooth muscle cells, can be used to increase the expression of ABC family members in the cells, e.g., SSG, ABC8, and ABC1, and thereby increase the transport of sterols, e.g., cholesterol, and other lipids across the membranes of the cells. LXR and RXR activation can be enhanced using any of a number of methods, preferably by administration of LXR or RXR agonists to the cells. Such methods are useful, e.g., for the treatment or prevention of any of the herein-described sterol-related disorders.

Modulators, recombinant forms, or fragments of SSG can be used to modulate sterol transport activity in cells, and can therefore be useful in the treatment or prevention of any of a large number of sterol, e.g., cholesterol, associated diseases and conditions, including, but not limited to, sitosterolemia, familial hypercholesterolemia, hyperlipidemia, atherosclerosis, coronary heart disease, HDL deficiencies, gall stones, nutritional deficiencies, and other cardiovascular diseases. It will be appreciated that the herein-described methods can be used either to increase or decrease the level of dietary sterol absorption. Thus, the present methods can be used to treat or prevent any condition associated with a sterol, e.g., cholesterol, deficiency by increasing the level of sterol absorption in patients affected with the condition. Modulation of SSG can also be used to modulate the development of foam cells, e.g., by modulating sterol, e.g., cholesterol retention in macrophages. In addition, modulators, recombinant forms, or fragments of SSG can be used to treat or prevent any sitosterolemia-associated condition such as arthritis, xanthomas, and chronic hemolytic anemia, in patients with sitosterolemia or in any other patient.

In numerous embodiments, the present invention provides methods of screening for modulators, e.g., activators, inhibitors, stimulators, enhancers, etc., of SSG nucleic acids and proteins. Such modulators can affect SSG activity in any of a number of ways, e.g., by modulating SSG transcription, translation, phosphorylation, mRNA or protein stability; by altering the binding of SSG to heterologous proteins or other molecules; by affecting SSG protein activity, or by modulating LXR or RXR activity. In preferred embodiments, modulators that enhance SSG activity or levels are used to treat any of the above-recited diseases and conditions.

In one embodiment, compounds are screened, e.g., using high throughput screening (HTS), to identify those compounds that can bind to and/or modulate the activity of an isolated SSG polypeptide or fragment thereof. In another embodiment, SSG proteins are recombinantly expressed in cells, and potential modulators of SSG are assayed by measuring an indicator of SSG activity, such as sterol transport activity.

In numerous embodiments, an SSG polynucleotide or polypeptide is introduced into a cell, in vivo or ex vivo, and the SSG activity in the cell is thereby modulated. For example, a polynucleotide encoding a full length SSG polypeptide is introduced into a population of cells, thereby increasing the level or activity of SSG in the cells. Alternatively, an antisense, ribozyme, or dominant-negative encoding polynucleotide can be introduced into a population of cells, thereby inhibiting the SSG, and associated sterol transport, in the cells.

The present invention also provides molecular tools for the diagnosis of sitosterolemia, e.g., by examining the nucleotide or amino acid sequence of SSG in a patient, or by examining the level of expression or activity of SSG in a patient. In addition, the present methods can be used to identify sitosterolemia-causing mutations in heterozygous carriers. In any of these embodiments, a detection of one or more mutations in an SSG gene that can diminish or alter the level of SSG protein or protein activity in a cell indicates that the patient has sitosterolemia, is at risk for sitosterolemia, or is a carrier of a sitosterolemia-causing allele. The detection of mutations in an SSG gene can also be used to detect the presence of or risk for developing any of the herein-described sterol-related disorders.

The present invention also provides methods for detecting SSG nucleic acid and protein expression, allowing investigation into SSG-associated sterol transport, and for detecting cells specifically involved in sterol transport. In addition, SSG nucleic acids and polypeptides provide useful markers for detecting LXR or RXR activity, e.g., to screen for LXR or RXR agonists. SSG also provides useful nucleic acid probes for paternity and forensic investigations. SSG polypeptides can also be used to generate monoclonal and polyclonal antibodies useful for identifying cells involved in cholesterol transport. SSG expression can be identified using techniques such as reverse transcription and amplification of mRNA, isolation of total RNA or poly $A^+$ RNA, northern blotting, dot blotting, in situ hybridization, RNase protection, S1 digestion, probing DNA microchip arrays, western blots, and the like.

Because the chromosome location of SSG in mice and in humans is known, the present invention also provides markers for chromosome mapping studies, e.g., for meiotic mapping studies to identify the location of nearby disease-causing genes.

Functionally, SSG nucleic acids encode transporter molecules that act in the transport of sterols, e.g., cholesterol, and other lipids across cell membranes. Such SSG polypeptides act to effect sterol transport in a large number of cells, including, but not limited to, cells of the liver, the intestine, in macrophages, and in smooth muscle cells. SSG belongs to the ABCG subfamily of transporters, and binds to ABC family members, e.g., ABC8, to effect cholesterol transport. Structurally, the nucleotide sequence of SSG (see, e.g., SEQ ID NOs:1 or 3, isolated from mice and humans, respectively) encodes polypeptides comprising one ATP binding domain, one hydrophobic domain (comprising six transmembrane regions), a motif A or P loop, a motif B, and other signature sequences typical of ABC transporters. Related SSG genes from other species share at least about 60% nucleotide sequence identity over a region of at least about 50 nucleotides in length, optionally 100, 200, 500, or more nucleotides in length, to SEQ ID NO:2 or 4, or encode polypeptides sharing at least about 60% amino acid sequence identity over an amino acid region at least about 25 amino acids in length, optionally 50 to 100 amino acids in length to SEQ ID NO:1 or 3. Preferably, the SSG polypeptide comprises at least about 650 amino acids. Typically, SSG polypeptides comprise an amino acid sequence at least about 80%, 90%, 95%, or 100%, identical to the amino acid sequences shown in SEQ ID NO:5 or SEQ ID NO:6.

The present invention also provides polymorphic variants of the SSG protein depicted in SEQ ID NO:1: variant #1, in which a leucine residue is substituted for an isoleucine residue at amino acid position 17; and variant #2, in which an alanine residue is substituted for a glycine residue at amino acid position 28.

The present invention also provides polymorphic variants of the SSG protein depicted in SEQ ID NO:3: variant #1, in which a lysine residue is substituted for an arginine residue at amino acid position 20; and variant #2, in which a valine residue is substituted for a leucine residue at amino acid position 26.

Specific regions of the SSG nucleotide and amino acid sequences may be used to identify polymorphic variants, interspecies homologs, and alleles of SSG genes. This identification can be made in vitro, e.g., under stringent hybridization conditions, or by PCR and sequencing, or by using the sequence information in a computer system for comparison with other nucleotide sequences. Typically, identification of polymorphic variants and alleles of SSG is made by comparing an amino acid sequence of about 25 amino acids or more, e.g., 50–100 amino acids. Amino acid identity of approximately at least 60% or above, optionally 65%, 70%, 75%, 80%, 85%, or 90–95% or above typically demonstrates that a protein is a polymorphic variant, interspecies homolog, or allele of SSG. Sequence comparison can be performed using any of the sequence comparison algorithms discussed below. Antibodies that bind specifically to SSG polypeptides or a conserved region thereof can also be used to identify alleles, interspecies homologs, and polymorphic variants.

Polymorphic variants, interspecies homologs, and alleles of SSG are confirmed by examining, e.g., interaction of the candidate variant, homolog, or allele to a heterologous ABC polypeptide, e.g., ABC8, or the cholesterol transporting ability of the putative SSG polypeptide. Typically, an SSG polypeptide having an amino acid sequence of SEQ ID NO:1 or SEQ ID NO:3 is used as a positive control in comparison to the putative SSG protein to demonstrate the identification of a polymorphic variant or allele of the SSG gene or protein.

Nucleotide and amino acid sequence information for SSG may also be used to construct models of SSG polypeptides in a computer system. These models are subsequently used to identify compounds that can activate or inhibit SSG proteins. Such compounds that modulate the activity of SSG genes or proteins can be used to investigate the role of SSG genes in, e.g., sterol transport in cell, and can also be used to treat or prevent any of the herein-described conditions and diseases.

The present invention also provides assays, preferably high throughput assays, to identify compounds or other molecules that interact with and/or modulate SSG. In certain assays, a particular domain of SSG is used, e.g., an ATP binding domain, a dimerization domain, or a transmembrane domain.

The present invention also provides methods to treat diseases or conditions associated with SSG activity. For example, SSG activity or expression can be altered in cells of a patient with any of a large number of disorders including, but not limited to, sitosterolemia, hypercholesterolemia, hyperlipidemia, atherosclerosis, xanthomas, arthritis, and hemolytic anemia. In such patients, increasing SSG in, e.g., intestinal, liver, or macrophage cells will enhance the efflux of sterol from the cells, thereby providing a treatment for the disorder. In addition, modulation of an SSG can be used to alter the amount and quality of sterols that are absorbed by a mammal from the diet. For example, increased SSG activity in cells of the intestine can be used to decrease or block the amount of dietary cholesterol and other sterols, including plant sterols, absorbed by the patient.

Transgenic animals and cells lacking one or more SSG alleles, or containing altered forms of SSG are also provided, as are kits for using the herein-disclosed polynucleotides and polypeptides and for practicing the herein-disclosed methods, are also provided.

II. Definitions

As used herein, the following terms have the meanings ascribed to them below unless specified otherwise.

As used herein, an "SSG protein" or "SSG polypeptide" refers to a transporter as shown in SEQ ID NO:1 or 3, or any derivative, homolog, or fragment thereof, and an "SSG polynucleotide" or SSG nucleic acid" or "SSG gene" refers to any nucleic acid encoding such a protein, derivative, homolog, or fragment thereof. SSG proteins or derivatives can be expressed in any cell type, including any eukaryotic or prokaryotic cell, or synthesized in vitro. Typically, SSG nucleic acids or genes encode transporters that associate with heterologous ABC transporter proteins, e.g., ABC8, to form a heterodimeric transporter that acts to transport cholesterol, other steroids, and other lipids out of cells. It will be recognized that derivatives, homologs, and fragments of SSG can readily be used in the present invention. Such SSG variants can comprise any one or more domains of the polypeptide shown as SEQ ID NO:1 or 3, or multiple copies of any one or more domains, or any number of domains in novel combinations with each other or with other proteins or protein domains. It is noted that SSG is used herein (and elsewhere) interchangeably with ABCG5.

The term "SSG" also refers to polymorphic variants, alleles, mutants, and interspecies homologs that: (1) have about 60% amino acid sequence identity, optionally about 75, 80, 85, 90, or 95% amino acid sequence identity to SEQ ID NO:1 or 3 over a window of about 25 amino acids, optionally 50–100 amino acids; (2) specifically bind to antibodies raised against an immunogen comprising an amino acid sequence of SEQ ID NO:1 or 3, and conservatively modified variants thereof, or (3) specifically hybridize (with a size of at least about 100, optionally at least about 500–1000 nucleotides) under stringent hybridization conditions to a sequence of SEQ ID NO:2 or 4, and conservatively modified variants thereof. Typically, "SSG" polypeptides include an amino acid sequence at least about 60%, 70%, 80%, 90%, 95%, or 100% identical to a sequence as set forth in SEQ ID NO:5 or SEQ ID NO:6.

Topologically, full-length SSG polypeptides include a "transport unit," an "ATP binding domain," "a hydrophobic domain" six "transmembrane regions," "motif A" or "P-loop," "motif B," and others. These domains can be structurally identified using methods known to those of skill in the art, such as standard sequence analysis programs and by comparison with related proteins. (see, e.g., Croop et al., *Methods in Enzymology* 292:101–162 (1998)). Additional domains can be readily identified using standard methods. For example, as SSG interacts with heterologous ABC family members, "dimerization domains" can be easily identified using standard methods to localize regions responsible for protein-protein interactions (e.g., cross-linking, deletion or mutation analysis, etc.).

An "ABC" protein, polypeptide, nucleic acid, polynucleotide, or gene refers to any member of the ABC superfamily of transporter molecules, or to any nucleic acid encoding an ABC transporter, or to any homolog, derivative, or variant of any of the transporters or nucleic acids. An "ABC" polypeptide includes any member of the superfamily, including whole site transporters, half site transporters, or to any subfamily within the superfamily, including subfamily A, B, C, D, E, F, or G, and can be derived from any organism, including prokaryotic and eukaryotic organisms. An "ABC" transporter can be involved in the transport of any compounds, including ions, drugs, peptides, and lipids, including sterols such as cholesterol.

"Biological sample," as used herein, refers to a sample of biological tissue or fluid that contains one or more SSG nucleic acids encoding one or more SSG proteins. Such samples include, but are not limited to, tissue isolated from humans and mice, in particular, intestine and liver. Biological samples may also include sections of tissues such as frozen sections taken for histological purposes. A biological sample is typically obtained from a eukaryotic organism, such as insects, protozoa, birds, fish, reptiles, and preferably a mammal such as rat, mouse, cow, dog, guinea pig, or rabbit, and most preferably a primate such as a chimpanzee or a human.

By "determining the functional effect" is meant assaying for a compound that modulates, e.g., increases or decreases, a parameter that is indirectly or directly under the influence of an SSG polypeptide, e.g., functional, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties, changes in gene expression of SSG or of any cellular activity, alterations of SSG binding to heterologous proteins or other molecules, and alterations in SSG activity, e.g., cholesterol transport.

"Inhibitors," "activators," and "modulators" of SSG genes or proteins are used interchangeably to refer to inhibitory, activating, or modulating molecules identified using in vitro and in vivo assays for SSG. Inhibitors are compounds that, e.g., bind to SSG proteins, partially or totally block SSG activity, downregulate SSG expression or stability, or prevent SSG binding to heterologous molecules, e.g., ABC8. Activators are compounds that, e.g., bind to SSG, stimulate SSG activity, increase SSG expression or stability, or facilitate SSG binding to membranes or to any other protein or factor, e.g., ABC8. Modulators may include genetically modified versions of SSG proteins, e.g., dominant negative or activated forms of SSG. Such assays for inhibitors and activators are described below and include, e.g., expressing SSG proteins in cells, applying putative modulator compounds, and then determining the functional effects of the putative modulator on SSG activity. Samples or assays comprising SSG polypeptides that are treated with a potential activator, inhibitor, or modulator are compared to control samples without the inhibitor, activator, or modulator to examine the effect of the candidate compound. Control samples (untreated with the compound) are typically assigned a relative SSG activity value of 100%. Inhibition of an SSG polypeptide is achieved when the activity value relative to the control is about 80%, optionally 50% or 25–0%. Activation of an SSG polypeptide is achieved when the activity value relative to the control is 110%, optionally 150%, optionally 200–500%, or 1000–3000% higher.

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated SSG nucleic acid is separated from open reading frames that flank the SSG gene and encode proteins other than SSG. The term "purified" denotes that a nucleic acid or protein gives rise to essentially one band in an electrophoretic gel. Particularly, it means that the nucleic acid or protein is at least 85% pure, optionally at least 95% pure, and optionally at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* (3$^{rd}$ ed., 1994) and Cantor and Schimmel, *Biophysical Chemistry Part I. The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or a "detectable moiety" is a composition detectable by spectroscopic, photochemical, biochemical, immunochemical, or chemical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are optionally directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 50 amino acids or nucleotides in length, or more preferably over a region that is 75–100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387–395 (1984)).

Another example of algorithm that is suitable for determining percent sequence identity and sequence similarity are the BLAST and BLAST 2.0 algorithms, which are described in Altschul et al., *Nuc. Acids Res.* 25:3389–3402 (1977) and Altschul et al., *J. Mol. Biol.* 215:403–410 (1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. Such washes can be performed for 5, 15, 30, 60, 120, or more minutes.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such washes can be performed for 5, 15, 30, 60, 120, or more minutes. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50–70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see, Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552–554 (1990)).

For preparation of monoclonal or polyclonal antibodies, any technique known in the art can be used (see, e.g., Kohler & Milstein, *Nature* 256:495–497 (1975); Kozbor et al., *Immunology Today* 4:72 (1983); Cole et al, pp. 77–96 in *Monoclonal Antibodies and Cancer Therapy* (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552–554 (1990); Marks et al., *Biotechnology* 10:779–783 (1992)).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

An "anti-SSG" antibody is an antibody or antibody fragment that specifically binds a polypeptide encoded by an SSG gene, cDNA, or a subsequence thereof.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to an SSG polypeptide from specific species such as rat, mouse, or human can be selected to obtain only those polyclonal antibodies that are specifically immunoreactive with the SSG protein and not with other proteins, except for polymorphic variants and alleles of the SSG protein. This selection may be achieved by subtracting out antibodies that cross-react with SSG molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

By "host cell" is meant a cell that contains an expression vector and supports the replication or expression of the expression vector. Host cells may be prokaryotic cells such as *E. coli,* or eukaryotic cells such as yeast, insect, amphibian, or mammalian cells such as CHO, HeLa and the like, e.g., cultured cells, explants, and cells in vivo.

III. Manipulation and Detection of SSG Nucleic Acids

In numerous embodiments of the present invention, nucleic acids encoding an SSG polypeptide, including a full-length SSG protein, or any derivative, variant, homolog, or fragment thereof, will be used. Such nucleic acids are useful for any of a number of applications, including for the production of SSG protein, for diagnostic assays, for therapeutic applications, for SSG specific probes, for assays for SSG binding and/or modulating compounds, to identify and/or isolate SSG homologs from other species, and other applications.

A. General Recombinant DNA Methods

Numerous applications of the present invention involve the cloning, synthesis, maintenance, mutagenesis, and other manipulations of nucleic acid sequences that can be performed using routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859–1862 (1981), using an automated synthesizer, as described in Van Devanter et al., *Nucleic Acids Res.* 12:6159–6168 (1984). Purification of oligonucleotides is by either native acrylamide gel electrophoresis or by anion-exchange HPLC as described in Pearson & Reanier, *J. Chrom.* 255:137–149 (1983).

The sequence of the cloned genes and synthetic oligonucleotides can be verified after cloning using, e.g., the chain termination method for sequencing double-stranded templates of Wallace et al., *Gene* 16:21–26 (1981).

B. Isolating and Detecting SSG Nucleotide Sequences

In numerous embodiments of the present invention, SSG nucleic acids will be isolated and cloned using recombinant methods. Such embodiments are used, e.g., to isolate SSG polynucleotides for protein expression or during the generation of variants, derivatives, expression cassettes, or other sequences derived from SSG, to monitor SSG gene expression, for the isolation or detection of SSG sequences in different species, for diagnostic purposes in a patient, i.e., to detect mutations in SSG, or for genotyping and/or forensic applications.

Often, the nucleic acid sequences encoding SSG proteins and related nucleic acid sequence homologs are cloned from cDNA and genomic DNA libraries by hybridization with probes, or isolated using amplification techniques with oligonucleotide primers. For example, SSG sequences are typically isolated from mammalian nucleic acid (genomic or cDNA) libraries by hybridizing with a nucleic acid probe, the sequence of which can be derived from SEQ ID NO:2 or 4, or amplified using primers designed from SEQ ID NO:2 or 4. A suitable biological material from which RNA and cDNA for SSG can be isolated is, e.g., intestine, liver, or macrophages.

Amplification techniques using primers can also be used to amplify and isolate SSG sequences from DNA or RNA (see, e.g., Dieffenfach & Dveksler, *PCR Primer: A Laboratory Manual* (1995)). Primers can be used, e.g., to amplify either the full length sequence or a probe of from one to several hundred nucleotides (using, e.g., primers designed from SEQ ID NOs: 2 or 4), which is then used to screen a mammalian library for full-length SSG clones.

Nucleic acids encoding SSG polypeptides can also be isolated from expression libraries using antibodies as probes. Such polyclonal or monoclonal antibodies can be raised using the sequence of SEQ ID NO:1 or 3, or derivatives or fragments thereof.

Polymorphic variants, alleles, and interspecies homologs that are substantially identical to an SSG gene can be isolated using SSG nucleic acid probes, and oligonucleotides under stringent hybridization conditions, by screening libraries. Alternatively, expression libraries can be used to clone SSG polymorphic variants, alleles, and interspecies homologs, by detecting expressed homologs immunologically with antisera or purified antibodies made against an SSG polypeptide, which also recognize and selectively bind to the SSG homolog.

More distantly related SSG homologs can be identified using any of a number of well known techniques, including by hybridizing an SSG probe with a genomic or cDNA library using moderately stringent conditions, or under low stringency conditions. Also, a distant homolog can be amplified from a nucleic acid library using degenerate primer sets, i.e., primers that incorporate all possible codons encoding a given amino acid sequence, in particular based on a highly conserved amino acid stretch. Such primers are well known by those of skill, and numerous programs are available, e.g., on the Internet, for degenerate primer design.

To make a cDNA library, one should choose a source that is rich in SSG mRNA, e.g., cells isolated from the intestine, the liver, or macrophage cells. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263–269 (1983); Sambrook et al., supra; Ausubel et al., supra).

For a genomic library, the DNA is extracted from the tissue or cells and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180–182 (1977). Colony hybridization is carried out as generally described in Grunstein et al., *Proc. Natl. Acad. Sci. USA.*, 72:3961–3965 (1975).

An alternative method of isolating SSG nucleic acid and its homologs combines the use of synthetic oligonucleotide primers and amplification of an RNA or DNA template (see, U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of SSG genes directly from mRNA, from cDNA, from genomic libraries or cDNA libraries. Degenerate oligonucleotides can be designed to amplify SSG homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of SSG-encoding mRNA in physiological samples, for nucleic acid sequencing, or for other purposes. Genes amplified by the PCR reaction can be purified from agarose gels and cloned into an appropriate vector.

Synthetic oligonucleotides can be used to construct recombinant SSG genes for use as probes or for expression of protein. This method is performed using a series of overlapping oligonucleotides usually 40–120 bp in length, representing both the sense and non-sense strands of the gene. These DNA fragments are then annealed, ligated and cloned. Alternatively, amplification techniques can be used with precise primers to amplify a specific subsequence of the SSG nucleic acid. The specific subsequence is then ligated into an expression vector.

The nucleic acid encoding an SSG polypeptide is typically cloned into intermediate vectors before transformation into prokaryotic or eukaryotic cells for replication and/or expression. These intermediate vectors are typically prokaryote vectors, e.g., plasmids, or shuttle vectors. Vectors, cells, and transfection methods are well known to those of skill and are described, e.g., in Ausubel or in Sambrook, both supra.

Optionally, nucleic acids will be used that encode chimeric proteins comprising an SSG polypeptide or domains thereof in combination with a heterologous polypeptide or polypeptides. For example, a domain such as an ATP binding domain, a transmembrane domain, a transport unit, or a dimerization domain, can be covalently linked to a heterologous protein such as a heterologous transmembrane domain, transport unit, etc. Other heterologous proteins of choice include a marker protein, e.g., luciferase, green fluorescent protein (GFP), and β-gal, each of which is well known in the art.

In certain embodiments, SSG polynucleotides will be detected using hybridization-based methods to determine, e.g., SSG RNA levels or to detect particular DNA sequences, e.g., for diagnosis, for genotyping, or for forensic applications. For example, gene expression of SSG can be analyzed by techniques known in the art, e.g., Northern blotting, reverse transcription and amplification of mRNA, dot blotting, in situ hybridization, RNase protection, probing DNA microchip arrays, and the like. In one embodiment, high density oligonucleotide analysis technology (e.g., GeneChip™) is used to identify homologs and polymorphic variants of SSG, or to monitor levels of SSG mRNA. In the case where a homolog is linked to a known disease, they can be used with GeneChip™ as a diagnostic tool in detecting the disease in a biological sample, see, e.g., Gunthand et al., *AIDS Res. Hum. Retroviruses* 14:869–876 (1998); Kozal et al, *Nat. Med.* 2:753–759 (1996); Matson et al., *Anal. Biochem.* 224:110–106 (1995); Lockhart et al., *Nat. Biotechnol.* 14:1675–1680 (1996); Gingeras et al., *Genome Res.* 8:435–448 (1998); Hacia et al., *Nucleic Acids Res.* 26:3865–3866 (1998).

In certain applications, an SSG DNA sequence will be detected, e.g., for diagnostic or forensic applications. For example, an SSG allele can be detected in a mammal using Southern blot hybridization, i.e., by isolating genomic DNA, performing a restriction digest on the isolated DNA, separating the restriction fragments electrophoretically, e.g., in an agarose gel, and transferring the separated DNA to a membrane and probing with a specific, labeled sequence. Southern blotting is well known to those of skill, and is taught in numerous sources, including Ausubel et al. and Sambrook et al.

In other embodiments, e.g., to detect tissue specific or temporal patterns of gene expression, an SSG polynucleotide is detected using in situ hybridization. In in situ hybridization, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4:230–250 (1986); Haase et al., *Methods in Virology,* vol. VII, pp. 189–226 (1984); and *Nucleic Acid Hybridization: A Practical Approach* (Hames et al., eds. 1987).

C. Expression in Prokaryotes and Eukaryotes

Often, a cloned SSG sequence will be expressed in a prokaryotic or eukaryotic cell to obtain expression, i.e., production of the encoded mRNA or protein. For example, in numerous embodiments, an SSG polynucleotide will be introduced into a cell to modulate the level of SSG activity in the cell, and thereby to modulate the level of cholesterol transport in cells of a patient, or dietary sterol absorption in the patient. To obtain high level expression of a cloned gene or nucleic acid, such as a cDNA encoding an SSG polypeptide, an SSG sequence is typically subcloned into an expression vector that contains a strong promoter to direct transcription, a transcription/translation terminator, and, if for a nucleic acid encoding a protein, a ribosome binding site for translational initiation. Suitable bacterial promoters are well known in the art and are described, e.g., in Sambrook et al. and Ausubel et al. Bacterial expression systems for expressing the SSG protein are available in, e.g., *E. coli, Bacillus* sp., and *Salmonella* (Palva et al., *Gene* 22:229–235 (1983); Mosbach et al., *Nature* 302:543–545 (1983). Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

For therapeutic applications, SSG nucleic acids are introduced into a cell, in vitro, in vivo, or ex vivo, using any of a large number of methods including, but not limited to, infection with viral vectors, liposome-based methods, biolistic particle acceleration (the gene gun), and naked DNA injection. Such therapeutically useful nucleic acids include, but are not limited to, coding sequences for full-length SSG, coding sequences for an SSG fragment, domain, derivative, or variant, SSG antisense sequences, and SSG ribozymes. Typically, such sequences will be operably linked to a promoter, but in numerous applications a nucleic acid will be administered to a cell that is itself directly therapeutically effective, e.g., certain antisense or ribozyme molecules.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the SSG-encoding nucleic acid in host cells. A typical expression cassette thus contains a promoter operably linked to the nucleic acid sequence encoding an SSG polypeptide, and signals required for efficient polyadenylation of the transcript, ribosome binding sites, and translation termination. The nucleic acid sequence encoding an SSG polypeptide may be linked to a cleavable signal peptide sequence to promote secretion of the encoded protein by the transfected cell. Such signal peptides would include, among others, the signal peptides from tissue plasminogen activator, insulin, and neuron growth factor, and juvenile hormone esterase of *Heliothis virescens.* Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc, HA-tag, 6-His (SEQ ID NO:44) tag, maltose binding protein, VSV-G tag, anti-DYKDDDDK (SEQ ID NO:45) tag, or any such tag, a large number of which are well known to those of skill in the art.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification, such as neomycin, thymidine kinase, hygromycin B phosphotransferase, and dihydrofolate reductase. Alternatively, high yield expression systems not involving gene amplification are also suitable, such as using a baculovirus vector in insect cells, with a sequence encoding an SSG polypeptide under the direction of the polyhedrin promoter or other strong baculovirus promoters.

The elements that are typically included in expression vectors also include a replicon that functions in *E. coli,* a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary.

Standard transfection methods are used to produce bacterial, mammalian, yeast or insect cell lines that express large quantities of an SSG protein, which are then purified using standard techniques (see, e.g., Colley et al., *J. Biol. Chem.* 264:17619–17622 (1989); *Guide to Protein Purification, in Methods in Enzymology,* vol. 182 (Deutscher, ed., 1990)). Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983).

Any of the well known procedures for introducing foreign nucleotide sequences into host cells may be used to introduce the expression vector. These include the use of reagents such as Superfect (Qiagen), liposomes, calcium phosphate transfection, polybrene, protoplast fusion, electroporation, microinjection, plasmid vectors, viral vectors, biolistic particle acceleration (the gene gun), or any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing an SSG gene.

After the expression vector is introduced into the cells, the transfected cells are cultured under conditions favoring expression of the SSG polypeptide, which is recovered from the culture using standard techniques identified below. Methods of culturing prokaryotic or eukaryotic cells are well known and are taught, e.g., in Ausubel et al., Sambrook et al., and in Freshney, *Culture of Animal Cells,* 3d. Ed., (1993), A Wiley-Liss Publication.

IV. Purification of SSG Polypeptides

Either naturally occurring or recombinant SSG polypeptides can be purified for use in functional assays, binding assays, diagnostic assays, and other applications. Optionally, recombinant SSG polypeptides are purified. Naturally occurring SSG polypeptides are purified, e.g., from mammalian tissue such as macrophages, liver, or intestine, or any other source of an SSG homolog. Recombinant SSG polypeptides are purified from any suitable bacterial or eukaryotic expression system, e.g., CHO cells or insect cells.

SSG proteins may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant SSG polypeptide is being purified. For example, proteins having established molecular adhesion properties can be reversibly fused to the SSG polypeptide. With the appropriate ligand, an SSG polypeptide can be selectively adsorbed to a purification column and then freed from the column in a relatively pure form. The fused protein is then removed by enzymatic activity. SSG proteins can also be purified using immunoaffinity columns.

A. Purification of SSG Protein from Recombinant Cells

Recombinant proteins are expressed by transformed bacteria or eukaryotic cells such as CHO cells or insect cells in large amounts, typically after promoter induction; but expression can be constitutive. Promoter induction with IPTG is one example of an inducible promoter system. Cells are grown according to standard procedures in the art. Fresh or frozen cells are used for isolation of protein.

Proteins expressed in bacteria may form insoluble aggregates ("inclusion bodies"). Several protocols are suitable for purification of SSG inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2–3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate) and 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. SSG polypeptides are separated from other bacterial proteins by standard separation techniques, e.g., with Ni-NTA agarose resin.

Alternatively, it is possible to purify SSG polypeptides from bacteria periplasm. After lysis of the bacteria, when an SSG protein is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying SSG Polypeptides

1. Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

2. Size Differential Filtration

The molecular weight of an SSG protein can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

3. Column Chromatography

SSG proteins can also be separated from other proteins on the basis of its size, net surface charge, hydrophobicity, and affinity for heterologous molecules. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

V. Antibodies to SSG Family Members

In numerous embodiments of the present invention, antibodies that specifically bind to SSG polypeptides will be used. Such antibodies have numerous applications, including for the modulation of SSG activity and for immunoassays to detect SSG, and variants, derivatives, fragments, etc. of SSG. Immunoassays can be used to qualitatively or quantitatively analyze the SSG polypeptide. A general overview of the applicable technology can be found in Harlow & Lane, *Antibodies. A Laboratory Manual* (1988).

Methods of producing polyclonal and monoclonal antibodies that react specifically with SSG polypeptides are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495–497 (1975)). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)).

A number of SSG-comprising immunogens may be used to produce antibodies specifically reactive with an SSG polypeptide. For example, a recombinant SSG protein, or an antigenic fragment thereof, is isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the SSG polypeptide. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-SSG proteins, or even related proteins from other organisms, using a competitive binding immunoassay. Specific polyclonal antisera and monoclonal antibodies will usually bind with a $K_d$ of at least about 0.1 mM, more usually at least about 1 µM, optionally at least about 0.1 µM or better, and optionally 0.01 µM or better.

Using SSG-specific antibodies, individual SSG proteins can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio, ed., 1980); and Harlow & Lane, supra.

A. Immunological Binding Assays

SSG proteins can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case an SSG protein or an antigenic subsequence thereof). The antibody (e.g., anti-SSG) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled SSG polypeptide or a labeled anti-SSG antibody. Alternatively, the labeling agent may be a third moiety, such a secondary antibody, that specifically binds to the antibody/SSG complex (a secondary antibody is typically specific to antibodies of the species from which the first antibody is derived). Other proteins capable of specifically binding immunoglobulin constant regions, such as protein A or protein G, may also be used as the label agent. These proteins exhibit a strong nonimmunogenic reactivity with immunoglobulin constant regions from a variety of species (see, e.g., Kronval et al., *J. Immunol.* 111: 1401–1406 (1973); Akerstrom et al., *J. Immunol.* 135:2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

1. Noncompetitive Assay Formats

Immunoassays for detecting an SSG protein in a sample may be either competitive or noncompetitive. Noncompetitive immunoassays are assays in which the amount of antigen is directly measured. In one preferred "sandwich" assay, for example, the anti-SSG antibodies can be bound directly to a solid substrate on which they are immobilized. These immobilized antibodies then capture the SSG protein present in the test sample. The SSG protein is thus immobilized is then bound by a labeling agent, such as a second SSG antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

2. Competitive Assay Formats

In competitive assays, the amount of SSG protein present in the sample is measured indirectly by measuring the amount of a known, added (exogenous) SSG protein displaced (competed away) from an anti-SSG antibody by the unknown SSG protein present in a sample. In one competitive assay, a known amount of SSG protein is added to a sample and the sample is then contacted with an antibody that specifically binds to the SSG protein. The amount of exogenous SSG protein bound to the antibody is inversely proportional to the concentration of SSG protein present in the sample. In a particularly preferred embodiment, the antibody is immobilized on a solid substrate. The amount of SSG protein bound to the antibody may be determined either by measuring the amount of SSG protein present in an SSG/antibody complex, or alternatively by measuring the amount of remaining uncomplexed protein. The amount of SSG protein may be detected by providing a labeled SSG molecule.

A hapten inhibition assay is another preferred competitive assay. In this assay the known SSG protein is immobilized on a solid substrate. A known amount of anti-SSG antibody is added to the sample, and the sample is then contacted with the immobilized SSG. The amount of anti-SSG antibody bound to the known immobilized SSG protein is inversely proportional to the amount of SSG protein present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

3. Cross-Reactivity Determinations

Immunoassays in the competitive binding format can also be used for crossreactivity determinations. For example, a protein at least partially encoded by SEQ ID NO:2 or 4 can be immobilized to a solid support. Proteins (e.g., SSG proteins and homologs) are added to the assay that compete for binding of the antisera to the immobilized antigen. The ability of the added proteins to compete for binding of the antisera to the immobilized protein is compared to the ability of the SSG polypeptide encoded by SEQ ID NO:2 or 4 to compete with itself. The percent cross-reactivity for the above proteins is calculated, using standard calculations. Those antisera with less than 10% cross-reactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of an SSG protein, to the immunogen protein (i.e., SSG protein encoded by SEQ ID NO:2 or 4). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by SEQ ID NO:2 or 4 that is required to inhibit 50% of binding, then the second protein is said to specifically bind to the polyclonal antibodies generated to an SSG immunogen.

Polyclonal antibodies that specifically bind to an SSG protein from a particular species can be made by subtracting out cross-reactive antibodies using SSG homologs. For example, antibodies specific to human SSG (SEQ ID NO:3) can be made by subtracting out antibodies that are cross-reactive with mouse SSG (SEQ ID NO:1). In an analogous fashion, antibodies specific to a particular SSG protein can be obtained in an organism with multiple SSG genes.

4. Other Assay Formats

Western blot (immunoblot) analysis is used to detect and quantify the presence of SSG protein in a sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the SSG protein. The anti-SSG polypeptide antibodies specifically bind to the SSG polypeptide on the solid support. These antibodies may be directly labeled or alternatively may be subsequently detected using labeled antibodies (e.g., labeled sheep anti-mouse antibodies) that specifically bind to the anti-SSG antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34–41 (1986)).

5. Reduction of Nonspecific Binding

One of skill in the art will appreciate that it is often desirable to minimize nonspecific binding in immunoassays. Particularly, where the assay involves an antigen or antibody immobilized on a solid substrate it is desirable to minimize the amount of nonspecific binding to the substrate. Means of reducing such nonspecific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

6. Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Nonradioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize an SSG protein, or secondary antibodies that recognize anti-SSG.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see, e.g., U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple calorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VI. Modulating SSG Activity in Cells

A. Assays for Modulators of SSG Proteins

In numerous embodiments of this invention, the level of SSG activity will be modulated in a cell by administering to the cell, in vivo or in vitro, any of a large number of SSG-modulating molecules, e.g., polypeptides, antibodies, amino acids, nucleotides, lipids, carbohydrates, or any organic or inorganic molecule. Such SSG modulators are particularly useful in the treatment of any of a large number of diseases and conditions.

To identify molecules capable of modulating SSG, assays will be performed to detect the effect of various compounds on SSG activity in a cell. Such assays can involve the identification of compounds that interact with SSG proteins, either physically or genetically, and can thus rely on any of a number of standard methods to detect physical or genetic interactions between compounds. Such assays can also involve the identification of compounds that affect SSG expression, activity or other properties, such as its phosphorylation or ability to bind other proteins. Such assays can also involve the detection of SSG activity in a cell, either in vitro or in vivo, and can thus involve the detection of, e.g., cholesterol transport into and out of a cell. Such cell-based assays can be performed in any type of cell, e.g., a cell that naturally expresses SSG, or a cultured cell that produces SSG due to recombinant expression.

It will be appreciated that any of the herein-described assays to identify modulators of SSG can also be used to identify modulators of LXR or RXR which, as described supra, regulate the expression of SSG and other ABC transporters. Such LXR and RXR transporters are thus useful for the treatment or prevention of any of the herein-described diseases and conditions.

B. Assays for SSG-Interacting Compounds

In certain embodiments, assays will be performed to identify molecules that physically or genetically interact with SSG proteins. Such molecules can be any type of molecule, including polypeptides, polynucleotides, amino acids, nucleotides, carbohydrates, lipids, or any other organic or inorganic molecule. Such molecules may represent molecules that normally interact with SSG to effect sterol transport, or may be synthetic or other molecules that are capable of interacting with SSG and that can potentially be used to modulate SSG activity in cells, or used as lead compounds to identify classes of molecules that can interact with and/or modulate SSG. Such assays may represent physical binding assays, such as affinity chromatography, immunoprecipitation, two-hybrid screens, or other binding assays, or may represent genetic assays as described infra.

In any of the binding or functional assays described herein, in vivo or in vitro, any SSG protein, or any derivative, variation, homolog, or fragment of an SSG protein, can be used. Preferably, the SSG protein is at least about 70% identical to SEQ ID NO:1 or 3. In numerous embodiments, a fragment of an SSG protein is used. For example, a fragment that contains only a transport unit, an ATP binding domain, a dimerization domain, a motif A, a motif B, a P loop, a transmembrane region, or any other subdomain or region of SSG, can be used. Such fragments can be used alone, in combination with other SSG fragments, or in combination with sequences from heterologous proteins, e.g., the fragments can be fused to a heterologous polypeptide, thereby forming a chimeric polypeptide.

1. Assays for Physical Interactions

Compounds that interact with SSG proteins can be isolated based on an ability to specifically bind to an SSG protein or fragment thereof. In numerous embodiments, the SSG protein or protein fragment will be attached to a solid support. In one embodiment, affinity columns are made using the SSG polypeptide, and physically-interacting molecules are identified. It will be apparent to one of skill that chromatographic techniques can be performed at any scale and using equipment from many different manufacturers (e.g., Pharmacia Biotech). In addition, molecules that interact with SSG proteins in vivo can be identified by co-immunoprecipitation or other methods, i.e., immunoprecipitating SSG proteins using anti-SSG antibodies from a cell or cell extract, and identifying compounds, e.g., proteins, that are precipitated along with the SSG protein. Such methods are well known to those of skill in the art and are taught, e.g., in Ausubel et al., Sambrook et al., Harlow & Lane, all supra.

Two-hybrid screens can also be used to identify polypeptides that interact in vivo with an SSG polypeptide or a fragment thereof (Fields et al., Nature 340:245–246 (1989)). Such screens comprise two discrete, modular domains of a transcription factor protein, e.g., a DNA binding domain and a transcriptional activation domain, which are produced in a cell as two separate polypeptides, each of which also comprises one of two potentially binding polypeptides. If the two potentially binding polypeptides in fact interact in vivo, then the DNA binding and the transcriptional activating domain of the transcription factor are united, thereby producing expression of a target gene in the cell. The target gene typically encodes an easily detectable gene product, e.g., β-galactosidase, GFP, or luciferase, which can be detected using standard methods. In the present invention, an SSG polypeptide is fused to one of the two domains of the transcription factor, and the potential SSG-binding polypeptides (e.g., encoded by a cDNA library) are fused to the other domain. Such methods are well known to those of skill in the art, and are taught, e.g., in Ausubel et al., supra.

In other preferred embodiments, an assay such as the fluorescence polarization assay or the fluorescence resonance energy transfer assay is employed to identify candidate modulators. These assays do not require the separation of bound and free labeled test compound. Fluorescence polarization (FP) or fluorescence anisotropy is a useful tool for the study of molecular interactions (see, e.g. http://www.panvera.com/tech/ appguide/fpintro.html, Nov. 4, 1999). First, a molecule labeled with a fluorophore is excited with plane polarized light. If the fluorescent molecule stays stationary while in the excited state, light is emitted in the same polarized plane. If the excited fluorescently labeled molecule rotates out of the plane of the polarized light while in the excited state, light is emitted from the molecule in a different plane. For example, if vertical polarized light is used to excite the fluorophore, the emission spectra can be monitored in the vertical and horizontal planes. Fluorescence polarization is calculated as shown in the following Formula I:

$$\text{Fluorescent polarization} = P = (\text{Int } \ddot{y} - \text{Int}\ddot{y})/(\text{Int } \ddot{y} + \text{Int}\ddot{y}) \quad \text{I}$$

In Formula I, Int ÿ is the intensity of the emission parallel to the excitation plane. Intÿ is the intensity of the emission perpendicular to the excitation plane.

A small fluorescently labeled molecule, when free in solution, can emit depolarized light when excited with the proper wavelength of light. If, however, the molecule (e.g., a ligand) binds to a second molecule (e.g., a receptor) the fluorescently labeled molecule is more constrained so the light emitted is more polarized and the fluorescence polarization (FP) value is higher. Thus, a higher FP value indicates that the fluorescently labeled molecule is able to bind to the second molecule. A competition assay also can be performed using FP. If an unlabeled molecule is present in the solution, then it will compete for binding to the second molecule, e.g., the antibody and the FP value will be decreased. Thus, FP can be used in competitive assays.

Commercial assays exist to test the affinity of compounds for human estrogen receptor using a fluorescently labeled estrogen compound (see, Panvera, (Madison, Wis.) publications Lit.#'s L0069, L0082, L0084, L0095, L0072, L0085). Similarly, test compounds can be fluorescently labeled with a fluorophore that is active in a FP assay. For example, N-terminal amines of proteins, peptide, or peptide analogs can be labeled with fluorescein (Panvera, publications Lit. # L0057 and L0059) or a small fluorescent compound. Briefly, a fluorescein-$C_6$-succinimidyl ester can be conjugated to peptides or proteins. The fluorescein labeled peptide/protein can then be purified from the unreacted fluorescein-C6-succinimidyl ester using thin-layer chromatography or gel filtration chromatography. If the labeled test compound can bind to a polypeptide that has an SSG binding domain, the level of polarization is increased.

Alternatively, a test compound can be screened for its ability to decrease the FP of a fluorescently labeled known SSG binding protein complexed with an SSG polypeptide. Briefly, a known SSG binding protein is labeled with a fluorescent moiety. A test compound that decreases the FP value of the fluorescently labeled SSG binding protein and SSG is displacing or inhibiting the ability of the fluorescently labeled SSG binding protein to bind to the SSG.

Methods employing the technique of fluorescence resonance energy transfer (FRET) can be employed using the methods and compositions of the present invention. FRET occurs between two fluorophores when the excitation of the donor fluorophore is transferred to the acceptor fluorophore. This interaction is dependent on the distance between the donor and acceptor fluorophore and distance-dependent interaction between a donor and acceptor molecule. The donor and acceptor molecules are fluorophores. If the fluorophores have excitation and emission spectra that overlap, then in close proximity (typically around 10–100 angstroms) the excitation of the donor fluorophore is transferred to the acceptor fluorophore. The relative proximity of the first and second labels is determined by measuring a change in the intrinsic fluorescence of the first or second label. Commonly, the emission of the first label is quenched by proximity of the second label.

Many appropriate interactive labels for FRET are known. For example, fluorescent labels, dyes, enzymatic labels, and antibody labels are all appropriate. Examples of preferred interactive fluorescent label pairs include terbium chelate and TRITC (tetrarhodamine isothiocyanate), europium cryptate and allophycocyanin and many others known to one of skill. Similarly, two colorimetric labels can result in combinations that yield a third color, e.g., a blue emission in proximity to a yellow emission produces an observed green emission.

With regard to preferred fluorescent pairs, there are a number of fluorophores which are known to quench each other. Fluorescence quenching is a bimolecular process that reduces the fluorescence quantum yield, typically without changing the fluorescence emission spectrum. Quenching can result from transient excited interactions, (collisional quenching) or, e.g., from the formation of nonfluorescent ground state species. Self-quenching is the quenching of one fluorophore by another; it tends to occur when high concentrations, labeling densities, or proximity of labels occurs. Some excited fluorophores interact to form excimers, which are excited state dimers that exhibit altered emission spectra (e.g., phospholipid analogs with pyrene sn-2 acyl chains); See Haugland (1996) *Handbook of Fluorescent Probes and Research Chemicals*, published by Molecular Probes, Inc., Eugene, Oreg.

The Forster radius ($R_o$) is the distance between fluorescent pairs at which energy transfer is 50% efficient (i.e., at which 50% of excited donors are deactivated by FRET). The magnitude of $R_o$ is dependent on the spectral properties of donor and acceptor dyes: $R_o=[8.8\times10^{23}\cdot K^2\cdot n^{-4}\cdot QY_D\cdot J(\ )]^{1/6}$ Å; where $K^2$=dipole orientation range factor (range 0 to 4, $K^2=\frac{2}{3}$ for randomly oriented donors and acceptors); $QY_D$= fluorescence quantum yield of the donor in the absence of the acceptor; n=refractive index; and J(1)=spectral overlap integral=$\ddot{y}_A(\ )\cdot F_D\cdot(4)d\ cm^3M^{-1}$, where A=extinction coefficient of acceptor and $F_D$=fluorescence emission intensity of donor as a fraction of total integrated intensity. Some typical $R_o$ are listed for typical donor acceptor pairs in Table 1:

TABLE 1

| Donor | Acceptor | $R_o$ (ÿ) |
|---|---|---|
| Fluorescein | Tetramethylrhodamine | 55 |
| IAEDANS | Fluorescein | 46 |
| EDANS | DABCYL | 33 |
| BODIPY FL | BODIPY FL | 57 |
| Fluorescein | QSY-7 dye | 61 |

An extensive compilation of $R_o$ values are found in the literature; see Haugland (1996), supra. In most uses, the donor and acceptor dyes are different, in which case FRET can be detected by the appearance of sensitized fluorescence of the acceptor or by quenching of the donor fluorescence. When the donor and acceptor are the same, FRET is detected by the resulting fluorescence depolarization.

In addition to quenching between fluorophores, individual fluorophores are also quenched by nitroxide-labeled molecules such as fatty acids. Spin labels such as nitroxides are also useful in the liquid phase assays of the invention.

Test compounds and an SSG polypeptide can be labeled with FRET pairs. If the test compound can directly interact with the SSG polypeptide, fluorescence resonance energy transfer can take place and the affinity can be measured. Alternatively, a known SSG binding protein can be labeled with an appropriate FRET label and incubated with an FRET fluorophore labeled polypeptide that includes an SSG. Fluorescence resonance energy transfer can take place between the labeled SSG binding protein and the labeled SSG. If a test compound were incubated with the two labeled components, the amount of FRET would be lowered if the test compound can inhibit or displace the binding of the labeled SSG binding protein to the SSG.

Additional methods for assaying the ability of test compounds to modulate SSG interactions with other proteins employ peptide sensors. These assays can be adapted from those described in WO 99/27365. Briefly, these assays use a peptide sensor to which is attached a detectable label. The peptides can be naturally occurring peptides that interact with SSG, or can be obtained through randomizing residues and selecting for binding to the SSG polypeptide. Panels of predetermined or randomized candidate sensors can be screened for SSG binding.

In typical embodiments, the sensor peptides are labeled with a detectable label. The detectable labels can be primary labels (where the label comprises an element that is detected directly or that produces a directly detectable element) or secondary labels (where the detected label binds to a primary label, as is common in immunological labeling). An introduction to labels, labeling procedures and detection of labels is found in Polak and Van Noorden (1997) *Introduction to Immunocytochemistry*, 2nd ed., Springer Verlag, N.Y. and in Haugland (1996) *Handbook of Fluorescent Probes and Research Chemicals*, a combined handbook and catalogue published by Molecular Probes, Inc., Eugene, Oreg. Primary and secondary labels can include undetected elements as well as detected elements. Useful primary and secondary labels in the present invention can include spectral labels such as fluorescent dyes (e.g., fluorescein and derivatives such as fluorescein isothiocyanate (FITC) and Oregon Green™, rhodamine and derivatives (e.g., Texas red, tetrarhodimine isothiocynate (TRITC), etc.), digoxigenin, biotin, phycoerythrin, AMCA, CyDyes™, and the like), radiolabels (e.g., 3H, 125I, 35S, 14C, 32P, 33P, etc.), enzymes (e.g., horse radish peroxidase, alkaline phosphatase etc.), spectral colorimetric labels such as colloidal gold or colored glass or plastic (e.g., polystyrene, polypropylene, latex, etc.) beads. The label may be coupled directly or indirectly to a component of the detection assay (e.g., the detection reagent) according to methods well known in the art. As indicated above, a wide variety of labels may be used, with the choice of label depending on sensitivity required, ease of conjugation with the compound, stability requirements, available instrumentation, and disposal provisions. In a presently preferred embodiment, the detectable label is a fluorescent label, in which case fluorescence polarization detection provides a sensitive and efficient means of detecting whether the peptide sensor is bound to the SSG polypeptide. See, e.g., Schindler et al. (1995) *Immunity* 2:689–697).

The sensor peptide and the SSG polypeptide are incubated under conditions that are suitable for sensor binding to the SSG polypeptide. In some embodiments, a candidate modulator of SSG binding to a corepressor, coactivator or other ligand is included in the reaction mixture. If a candidate modulator increases or decreases binding of the sensor peptide to the SSG polypeptide, the candidate modulator is a potential lead compound for modulating SSG-mediated sterol transport in cells.

C. Assays for SSG Protein Activity

SSG genes and their alleles and polymorphic variants encode transporters that promote the translocation of cholesterol and other sterols, as well as other lipids, across cell membranes, e.g., from the cytoplasm to the cell exterior. Accordingly, the activity of SSG polypeptides can be assessed using a variety of in vitro and in vivo assays to determine functional, chemical, and physical effects, e.g., directly measuring the cholesterol or other lipid transport into and out of cells, measuring SSG protein and/or RNA levels, or measuring other aspects of SSG polypeptides, e.g., phosphorylation levels, transcription levels, and the like. Such assays can be used to test for both activators and inhibitors of SSG proteins. Modulators can also be genetically altered versions of SSG proteins, e.g., dominant negative forms of SSG or of proteins that interact with SSG, e.g., ABC8. Such modulators of activity are useful for, e.g., many diagnostic and therapeutic applications.

Any assays for cholesterol transport can be used in the present invention. For example, to assess the level of cholesterol (or other sterol or lipid) efflux in cells in culture, radioactively labeled cholesterol, e.g., $^{14}$C-cholesterol, is added to culture medium, and the amount of labeled cholesterol in the cell (e.g., in cell lysates) or outside of the cell (e.g., in culture medium) in the presence or absence of a test agent is detected. (see, e.g., Klucken et al., (2000) *PNAS* 97:817–822).

Other, animal-based models of SSG activity can also be used. For example, a given amount of radiolabeled $^{14}$C-cholesterol is added to the diet of a mammal that also contains a test agent. The ability of the test agent to affect the level of cholesterol absorption is then assayed by monitoring the amount of labeled cholesterol taken up by the intestine of the mammal. In addition, the ability of any test agent can be assessed by virtue of an alteration in any characteristic of sitosterolemia, e.g., atherosclerosis, xanthomas, arthritis, chronic hemolytic anemia, etc.

The SSG protein of any of the herein-described assays will typically be a recombinant or naturally occurring polypeptide with a sequence of SEQ ID NO:1 or 3 or conservatively modified variants thereof. Alternatively, the SSG protein of the assay will be derived from a eukaryote and include an amino acid subsequence having amino acid sequence identity to SEQ ID NO:1 or 3. Generally, the amino acid sequence identity will be at least 60%, optionally at least 70% to 85%, optionally at least 90–95%. Optionally, the polypeptide of the assays will comprise a domain of an SSG protein, such as a transport unit, ATP binding domain, or transmembrane domain. In certain embodiments, a domain of an SSG protein is bound to a solid substrate and used, e.g., to isolate any molecules that can bind to and/or modulate their activity. In certain embodiments, a domain of an SSG polypeptide is fused to a heterologous polypeptide, thereby forming a chimeric polypeptide. Such chimeric polypeptides are also useful, e.g., in assays to identify modulators of SSG.

Samples or assays that are treated with a potential SSG protein inhibitor or activator are compared to control samples without the test compound, to examine the extent of modulation. Control samples (untreated with activators or inhibitors) are assigned a relative SSG activity value of 100. Inhibition of an SSG protein is achieved when the SSG activity value relative to the control is about 90%, optionally 50%, optionally 25–0%. Activation of an SSG protein is achieved when the SSG activity value relative to the control is 110%, optionally 150%, 200–500%, or 1000–2000%.

The effects of the test compounds upon the function of the polypeptides can be measured by examining any of the parameters described above. Any suitable physiological change that affects SSG activity can be used to assess the influence of a test compound on the polypeptides of this invention.

In another preferred embodiment, a "knock-in" assay is used in which the coding sequence for a marker gene, e.g., luciferase or GFP, is used to replace, e.g., by homologous recombination, the coding sequence for a gene of interest, e.g., SSG, in a cell. In this way, the marker gene serves as a direct reporter for the expression of the gene of interest. In a typical such embodiment, a coding sequence for an SSG gene is replaced by homologous recombination with a coding sequence for luciferase in a mammalian cell. The cell is then exposed to a test agent and the expression of the luciferase is detected, preferably in a homogeneous format, most preferably using high throughput screening methods.

D. Modulators and Binding Compounds

The compounds tested as modulators of an SSG protein can be any small chemical compound, or a biological entity, such as a protein, sugar, nucleic acid or lipid. Alternatively, modulators can be genetically altered versions of a SSG gene. Typically, test compounds will be small chemical molecules and peptides. Essentially any chemical compound can be used as a potential modulator or binding compound in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In one preferred embodiment, high throughput screening methods involve providing a combinatorial chemical or peptide library containing a large number of potential therapeutic compounds (potential modulator or binding compounds). Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217–9218 (1992)), analogous organic syntheses of small compound libraries (Chen et al, *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309–314 (1996) and PCT/US96/10287), carbohydrate libraries (see, e.g., Liang et al., *Science,* 274:1520–1522 (1996) and U.S. Pat. No. 5,593,853), small organic molecule libraries (see, e.g., benzodiazepines, Baum C&EN, Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

1. Solid State and Soluble High Throughput Assays

In one embodiment, the invention provides soluble assays using an SSG polypeptide, or fragment thereof, either alone or covalently linked to a heterologous protein to create a chimeric molecule. In another embodiment, the invention provides solid phase based in vitro assays in a high throughput format, where a domain, chimeric molecule, SSG protein, or cell or tissue expressing an SSG protein is attached to a solid phase substrate.

In the high throughput assays of the invention, it is possible to screen up to several thousand different modulators in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000–20,000 different compounds is possible using the integrated systems of the invention. More recently, microfluidic approaches to reagent manipulation have been developed.

The molecule of interest can be bound to the solid state component, directly or indirectly, via covalent or non covalent linkage, e.g., via a tag. The tag can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly-gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149–2154 (1963) (describing solid phase synthesis of, e.g., peptides); Geysen et al., *J. Immun. Meth.* 102:259–274 (1987) (describing synthesis of solid phase components on pins); Frank & Doring, *Tetrahedron* 44:6031–6040 (1988) (describing synthesis of various peptide sequences on cellulose disks); Fodor et al., *Science,* 251:767–777 (1991); Sheldon et al., *Clinical Chemistry* 39(4):718–719 (1993); and Kozal et al., *Nature Medicine* 2(7):753759 (1996) (all describing arrays of biopolymers fixed to solid substrates). Nonchemical approaches for fixing tag binders to substrates include other common methods, such as heat, cross-linking by UV radiation, and the like.

2. Computer-Based Assays

Yet another assay for compounds that modulate SSG protein activity involves computer assisted drug design, in which a computer system is used to generate a three-dimensional structure of an SSG protein based on the structural information encoded by its amino acid sequence. The input amino acid sequence interacts directly and actively with a pre-established algorithm in a computer program to yield secondary, tertiary, and quaternary structural models of the protein. The models of the protein structure are then examined to identify regions of the structure that have the ability to bind. These regions are then used to identify compounds that bind to the protein.

The three-dimensional structural model of the protein is generated by entering protein amino acid sequences of at least 10 amino acid residues or corresponding nucleic acid sequences encoding an SSG polypeptide into the computer system. The nucleotide sequence encoding the polypeptide preferably comprises SEQ ID NO:2 or SEQ ID NO:4, and conservatively modified versions thereof. The amino acid sequence, preferably comprising SEQ ID NO:1 or 3, or conservatively modifies versions thereof, represents the primary sequence or subsequence of the protein, which encodes the structural information of the protein. At least 10 residues of the amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art.

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential modulator binding regions are identified by the computer system. Three-dimensional structures for potential modulators are generated by entering amino acid or nucleotide sequences or chemical formulas of compounds, as described above. The three-dimensional structure of the potential modulator is then compared to that of the SSG protein to identify compounds that bind to the protein. Binding affinity between the protein and compound is determined using energy terms to determine which compounds have an enhanced probability of binding to the protein.

Computer systems are also used to screen for mutations, polymorphic variants, alleles and interspecies homologs of SSG genes. Such mutations can be associated with disease states or genetic traits. As described above, GeneChip™ and related technology can also be used to screen for mutations, polymorphic variants, alleles and interspecies homologs. Once the variants are identified, diagnostic assays can be used to identify patients having such mutated genes. Identification of the mutated SSG genes involves receiving input of a first nucleic acid sequence of SEQ ID NO:2 or 4, or a first amino acid sequence of SEQ ID NO:1 or 3, and conservatively modified versions thereof. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in various SSG genes, and mutations associated with disease states and genetic traits.

VII. Modulating SSG Activity/Expression to Treat Diseases or Conditions.

In numerous embodiments of this invention, a compound, e.g., nucleic acid, polypeptide, or other molecule is administered to a patient, in vivo or ex vivo, to effect a change in SSG activity or expression in the patient. Such compounds can be nucleic acids encoding full length SSG polypeptides, e.g., as shown as SEQ ID NO:1 or 3, or any derivative, fragment, or variant thereof, operably linked to a promoter. Suitable nucleic acids also include inhibitory sequences such as antisense or ribozyme sequences, which can be delivered in, e.g., an expression vector operably linked to a promoter, or can be delivered directly. Also, any nucleic acid that encodes a polypeptide that modulates the expression of SSG can be used. In general, nucleic acids can be delivered to cells using any of a large number of vectors or methods, e.g., retroviral, adenoviral, or adeno-associated virus vectors, liposomal formulations, naked DNA injection, and others. All of these methods are well known to those of skill in the art.

Proteins can also be delivered to a patient to modulate SSG activity. In preferred embodiments, a polyclonal or monoclonal antibody that specifically binds to SSG, particularly to an ATP binding domain, a tranport unit, or a dimerization domain, will be delivered. In addition, any polypeptide that interacts with and/or modulates SSG activity can be used, e.g., a polypeptide that is identified using the presently described assays, or any dominant negative form of SSG or an SSG-interacting protein, e.g., ABC8, etc. In addition, any polypeptides that affect SSG expression can be used.

Further, any compound that is found to or designed to interact with and/or modulate the activity of SSG can be used. For example, any compound that is found, using the methods described herein, to bind to or modulate the activity of SSG can be used.

In a preferred embodiment, a compound that affects the activity of an RXR-LXR heterodimer is used. For example, an LXR agonist can be administered to the cell, thereby causing an increase in the expression of SSG as well as other ABCs such as ABC8. Such LXR agonists include, e.g., cholesterol as well as synthetic compounds such as Compounds A, B, C, and others, which are described in U.S. patent application Ser. Nos., the teachings of which are herein incorporated by reference. Alternatively, RXR agonists can be used. In other embodiments, nucleic acids encoding LXR or RXR can be introduced into cells of interest, thereby causing an increase in the level of LXR-RXR activity, and thereby causing an increase in SSG-mediated transport activity. Additional LXR agonists can be identified using assays as described in U.S. application Ser. Nos. 60/115,292, 60/124,525, 09/525861, and 09/479315, and in TTC Reference Nos. 018781-003010 and 018781-003310, and using any of the biochemical, genetic, or cell-based assays described herein.

Any of the above-described molecules can be used to increase or decrease the expression or activity of SSG, or to otherwise affect the properties and/or behavior of SSG polypeptides or polynucleotides, e.g., stability, phosphorylation, kinase activity, interactions with other proteins, etc. The present compounds can thus be used to treat any of a number of diseases, including, but not limited to, sitosterolemia, atherosclerosis, hyperlipidemia, gall stones (e.g., cholesterol stones) hypercholesterolemia (e.g., familial hypercholesterolemia) coronary heart disease, HDL deficiency, nutritional deficiency, arthritis, xanthomas, and hemolytic anemia.

The present methods can also be used simply to lower the amount of cholesterol and other sterols absorbed in the diet of any mammal, to lower the amount of cholesterol retained in the liver of any mammal, and to prevent the formation of foam cells in a mammal, thereby preventing the development of the above-described diseases and conditions in any mammal. Further, such compounds can be administered specifically to one or another cell type, for example, specifically to cells lining the intestinal lumen, thereby preventing absorption of dietary cholesterol and other sterols, or specifically to macrophage cells, e.g., in the vicinity of an atherosclerotic plaque, thereby inhibiting the development of foam cells. Such cells can be targeted in any of a number of well known ways, for example by local administration of the compound, or by delivering the compound in combination with a moiety that can specifically target the compound to the cell of interest, e.g., a cell specific antibody or ligand.

A. Administration and Pharmaceutical Compositions

Administration of any of the present molecules can be achieved by any of the routes normally used for introducing a modulator compound into ultimate contact with the tissue to be treated. The modulators are administered in any suitable manner, optionally with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, 17$^{th}$ ed. 1985)).

The SSG modulators, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for administration include aqueous and nonaqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, intravesically or intrathecally. The formulations of compounds can be presented in unit-dose or multi-dose sealed containers, such as ampules and vials. Solutions and suspensions can be prepared from sterile powders, granules, and tablets of the kind previously described. The modulators can also be administered as part a of prepared food or drug.

The dose administered to a patient, in the context of the present invention should be sufficient to effect a beneficial response in the subject over time. The dose will be determined by the efficacy of the particular modulators employed and the condition of the subject, as well as the body weight or surface area of the area to be treated. The size of the dose also will be determined by the existence, nature, and extent of any adverse side-effects that accompany the administration of a particular compound or vector in a particular subject.

In determining the effective amount of the modulator to be administered, a physician may evaluate circulating plasma levels of the modulator, modulator toxicities, and the production of anti-modulator antibodies. In general, the dose equivalent of a modulator is from about 1 ng/kg to 10 mg/kg for a typical subject.

For administration, modulators of the present invention can be administered at a rate determined by the LD-50 of the modulator, and the side-effects of the compound at various concentrations, as applied to the mass and overall health of the subject. Administration can be accomplished via single or divided doses.

VIII. Transgenic Animals

Transgenic and chimeric non-human mammals and methods for generating them are described below. The mammals are useful, inter alia, for testing the function of SSG in vivo, to generate models for the study of cholesterol-associated diseases and conditions, and for the development of potential treatments for SSG related diseases and conditions, such as sitosterolemia and other cardiovascular disorders.

Transgenic and chimeric non-human mammals are generated that contain cells that lack at least one functional endogenous allele for SSG. A "chimeric animal" includes some cells that lack the functional SSG gene of interest and other cells that do not have the inactivated gene. A "transgenic animal," in contrast, is made up of cells that have all incorporated the specific modification which renders the SSG gene inactive or otherwise altered. While a transgenic animal is typically always capable of transmitting the mutant SSG gene to its progeny, the ability of a chimeric animal to transmit the mutation depends upon whether the inactivated gene is present in the animal's germ cells. The modifications that inactivate or otherwise alter the SSG gene can include, for example, insertions, deletions, or substitutions of one or more nucleotides. The modifications can interfere with transcription of the gene itself, with translation and/or stability of the resulting mRNA, or can cause the gene to encode an inactive or otherwise altered SSG polypeptide, e.g., an SSG polypeptide with modified binding properties or transport activity.

The claimed methods are useful for producing transgenic and chimeric animals of most vertebrate species. Such species include, but are not limited to, nonhuman mammals, including rodents such as mice and rats, rabbits, ovines such as sheep and goats, porcines such as pigs, and bovines such as cattle and buffalo. Methods of obtaining transgenic animals are described in, for example, Puhler, A., Ed., *Genetic Engineering of Animals*, VCH Publ., 1993; Murphy and Carter, Eds., *Transgenesis Techniques: Principles and Protocols* (*Methods in Molecular Biology*, Vol. 18), 1993; and Pinkert, C A, Ed., *Transgenic Animal Technology: A Laboratory Handbook*, Academic Press, 1994.

In preferred embodiments, transgenic mice will be produced as described in Thomas et al., (1999) *Immunol.* 163:978–84; Kanakaraj et al. (1998) *J. Exp. Med.* 187:2073–9; or Yeh et al., (1997) *Immunity* 7:715–725.

Typically, a modified SSG gene is introduced, e.g., by homologous recombination, into embryonic stem cells (ES), which are obtained from preimplantation embryos and cultured in vitro. See, e.g., Hooper, M L, *Embryonal Stem Cells: Introducing Planned Changes into the Animal Germline* (Modern Genetics, v.1), Int'l. Pub. Distrib., Inc., 1993; Bradley et al. (1984) *Nature* 309:255–258. Subsequently, the transformed ES cell is combined with a blastocyst from a non-human animal, e.g., a mouse. The ES cells colonize the embryo and in some embryos form the germ line of the resulting chimeric animal. See, Jaenisch (1988) *Science* 240:1468–1474. Alternatively, ES cells or somatic cells that can reconstitute an organism ("somatic repopulating cells") can be used as a source of nuclei for transplantation into an enucleated fertilized oocyte giving rise to a transgenic mammal. See, e.g., Wilmut et al. (1997) *Nature* 385:810–813.

Other methods for obtaining a transgenic or chimeric animal having a mutant SSG gene in its genome is to contact fertilized oocytes with a vector that includes a polynucleotide that encodes a modified, e.g., inactive, SSG polypeptide. In some animals, such as mice, fertilization is typically performed in vivo and fertilized ova are surgically removed. In other animals, particularly bovines, it is preferably to remove ova from live or slaughterhouse animals and fertilize the ova in vitro. See, DeBoer et al., WO 91/08216. In vitro fertilization permits the modifications to be introduced into substantially synchronous cells.

Fertilized oocytes are typically cultured in vitro until a pre-implantation embryo is obtained containing about 16–150 cells. The 16–32 cell stage of an embryo is described as a morula, whereas pre-implantation embryos containing more than 32 cells are termed blastocysts. These embryos show the development of a blastocoel cavity, typically at the 64 cell stage. The presence of a desired SSG mutation in the cells of the embryo can be detected by methods known to those of skill in the art, e.g., Southern blotting, PCR, DNA sequencing, or other standard methods. Methods for culturing fertilized oocytes to the pre-implantation stage are described, e.g., by Gordon et al. (1984) *Methods Enzymol.* 101:414; Hogan et al. *Manipulation of the Mouse Embryo: A Laboratory Manual*, C.S.H.L. N.Y. (1986) (mouse embryo); Hammer et al. (1985) *Nature* 315:680 (rabbit and porcine embryos); Gandolfi et al. (1987) *J. Reprod. Fert.* 81:23–28; Rexroad et al. (1988) *J. Anim. Sci.* 66:947–953 (ovine embryos) and Eyestone et al. (1989) *J. Reprod. Fert.* 85:715–720; Camous et al. (1984) *J. Reprod. Fert.* 72:779–785; and Heyman et al. (1987) *Theriogenology* 27:5968 (bovine embryos). Pre-implantation embryos may also be stored frozen for a period pending implantation.

Pre-implantation embryos are transferred to an appropriate female resulting in the birth of a transgenic or chimeric animal, depending upon the stage of development when the transgene is integrated. Chimeric mammals can be bred to form true germline transgenic animals. Chimeric mice and germline transgenic mice can also be ordered from commercial sources (e.g., Deltagen, San Carlos, Calif.).

Other methods for introducing mutations into mammalian cells or animals include recombinase systems, which can be employed to delete all or a portion of a locus of interest. Examples of recombinase systems include, the cre/lox system of bacteriophage P1 (see, e.g., Gu et al. (1994) *Science* 265:103–106; Terry et al. (1997) *Transgenic Res.* 6:349–356) and the FLP/FRT site specific integration system (see, e.g., Dymecki (1996) *Proc. Natl. Acad. Sci. USA* 93:6191–6196). In these systems, sites recognized by the particular recombinase are typically introduced into the genome at a position flanking the portion of the gene that is to be deleted. Introduction of the recombinase into the cells then catalyzes recombination which deletes from the genome the polynucleotide sequence that is flanked by the recombination sites. If desired, one can obtain animals in which only certain cell types lack the SSG gene of interest, e.g., by using a tissue specific promoter to drive the expression of the recombinase. See, e.g., Tsien et al. (1996) *Cell* 87:1317–26; Brocard et al. (1996) *Proc. Natl. Acad. Sci. USA* 93:10887–10890; Wang et al. (1996) *Proc. Natl. Acad. Sci. USA* 93:3932–6; Meyers et al. (1998) *Nat. Genet.* 18:136–41).

The presence of any mutation in an SSG gene in a cell or animal can be detected using any method described herein, e.g., Southern blot, PCR, or DNA sequencing. See, e.g., Ausubel et al., supra.

IX. Kits

SSG genes and their homologs are useful tools for a number of applications, including, but not limited to, diagnosing sitosterolemia and other cardiovascular disorders, for forensics and paternity determinations, and for treating any of a large number of SSG associated diseases. SSG specific reagents that specifically hybridize to SSG nucleic acids, such as SSG probes and primers, and SSG specific reagents that specifically bind to or modulate the activity of an SSG protein, e.g., SSG antibodies or other compounds can thus be provided in a kit for the practice of any of the applications described herein.

Nucleic acid assays for the presence of DNA and RNA for a SSG polynucleotide in a sample include numerous techniques known to those skilled in the art, such as Southern analysis, Northern analysis, dot blots, RNase protection, S1 analysis, amplification techniques such as PCR and LCR, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4:230–250 (1986); Haase et al., *Methods in Virology*, vol. VII, pp. 189–226 (1984); and *Nucleic Acid Hybridization: A Practical Approach* (Hames et al, eds. 1987). In addition, an SSG protein can be detected with the various immunoassay techniques described above. The test sample is typically compared to both a positive control (e.g., a sample expressing a recombinant SSG protein) and a negative control.

The present invention also provides kits for screening for modulators of SSG proteins or nucleic acids. Such kits can be prepared from readily available materials and reagents. For example, such kits can comprise any one or more of the following materials: SSG nucleic acids or proteins, reaction tubes, and instructions for testing SSG activity. Optionally, the kit can contain a biologically active SSG protein. A wide variety of kits and components can be prepared according to the present invention, depending upon the intended user of the kit and the particular needs of the user.

X. EXAMPLES

A. Gene Expression Microarray (GEM) Analysis

This example describes the identification of genes that are highly upregulated in intestinal cells following exposure to the LXRα agonist Compound A.

Total RNA was prepared from untreated (control) and treated (50 mg/kg of LXRα agonist Compound A) C57BL/6 mouse liver, intestine and kidney. Control and treated RNA samples were used to generate separate pools of unique, fluorescently labeled cDNA probes (performed at Incyte Genomics Inc.). Each (two fluorescent probe) tissue sample was simultaneously applied to a single Incyte Mouse GEM™ 1 microarray where they were competitively reacted with the arrayed cDNA molecules (containing 8,734 cDNA elements). The intensity of the fluorescence at each array element is proportional to the expression level of that particular gene in the sample. Each element of the GEM™ microarray was scanned for the first fluorescent color, and then repeated for the second fluorescent label. The ratio of the two fluorescent intensities provided a quantitative measurement of the relative gene expression level in the two samples. Data analysis on the fluorescent intensities resulted in a compilation of the 8,734 genes and their relative expression levels in the treated and untreated animals. A portion of that composite is shown in Table 2, which lists genes having the highest relative expression levels in the treated intestine and their corresponding relative expression levels in liver and kidney. Genes that were upregulated by LXR agonist treatment are represented by positive (+) values and those with diminished expression levels relative to untreated controls appear as negative (−). One EST in particular, corresponding to Accession Number AA237916, and shown in the first row of Table 2, was selected for further analysis, in part based on its similarity to the *Drosophila* Brown protein, a member of the ABC superfamily.

TABLE 2

Genes highly upregulated in intestine following treatment with the LXR agonist Compound A
GEM ANALYSIS: MOUSE INTESTINE, LIVER AND KIDNEY WITH LXR AGONIST COMPOUND A

| Accession Num | Intestine | Liver | Kidney | GeneName |
|---|---|---|---|---|
| AA237916 | 2.5 | 2.4 | −1.1 | ESTs, Weakly similar to BROWN PROTEIN [*D.melanogaster*] {IMAGE:680198} |
| AA476158 | 2.5 | 2.4 | 1.9 | Mus musculus transcription factor GIF mRNA, complete cds {IMAGE:876145} |
| AA060526 | 2 | 1.3 | −1.3 | ESTs, Moderately similar to COLIPASE PRECURSOR [*Rattus norvegicus*] {IMAGE:481341} |
| W97092 | 2 | −1.3 | 1 | ESTs {IMAGE:418790} |
| AA152947 | 2.2 | ? | ? | IMAGE EST {IMAGE:583833} |
| AA162935 | 1.8 | 1.7 | −1.1 | IMAGE EST {IMAGE:583311} |
| AA389271 | 1.9 | 1.3 | 1.5 | IMAGE EST {IMAGE:749897} |
| AA097341 | 1.6 | 1.2 | 1.1 | Mus musculus steroid receptor coactivator-1 (mSRC-1) mRNA, complete cds {IMAGE:523588} |
| AA245078 | 1.6 | 1.5 | −1.2 | Fatty acid binding protein intestinal {IMAGE:679661} |
| AA267525 | 1.6 | 2 | 1.4 | Carnitine palmitoyltransferase 1, liver {IMAGE:717056} |
| AA277507 | 1.6 | 1.7 | 2.4 | IMAGE EST {IMAGE:737620} |
| AA245078 | 1.6 | 1.5 | −1.2 | Fatty acid binding protein intestinal {IMAGE:679661} |
| AA067346 | 1.6 | 1.6 | 1.3 | IMAGE EST {IMAGE:523726} |
| AA389278 | 1.5 | 1.5 | 1.4 | ESTs {IMAGE:749926} |
| AA396418 | 1.5 | 1.5 | 1.2 | ESTs {IMAGE:750129} |
| W97311 | 1.5 | 1.6 | 1.5 | IMAGE EST {IMAGE:423203} |
| AA004183 | 1.5 | 1.4 | 1.2 | Receptor-like tyrosine kinase {IMAGE:439496} |
| AA213017 | 1.5 | 3.8 | 1.1 | Mus musculus flavin-containing monooxygenase 3 mRNA, complete cds {IMAGE:677605} |
| AA537107 | 1.5 | 1.5 | 1.5 | IMAGE EST {IMAGE:949512} |

TABLE 2-continued

Genes highly upregulated in intestine following treatment with the LXR agonist Compound A
GEM ANALYSIS: MOUSE INTESTINE, LIVER AND KIDNEY WITH LXR AGONIST COMPOUND A

| Accession Num | Intestine | Liver | Kidney | GeneName |
|---|---|---|---|---|
| AA537291 | 1.5 | 1.6 | 1.7 | IMAGE EST {IMAGE:949644} |
| AA014102 | 1.5 | 1.6 | −1 | IMAGE EST {IMAGE:443916} |
| AA030193 | 1.5 | 1.5 | 1.1 | Mus musculus mRNA for glycoprotein-associated amino acid transporter y + LAT1 b {IMAGE:457955} |
| AA034840 | 1.5 | 1.7 | −1.1 | IMAGE EST {IMAGE:467182} |
| AA034840 | 1.5 | 1.7 | −1.1 | IMAGE EST {IMAGE:467182} |
| W85526 | 1.4 | 1.6 | 1.2 | IMAGE EST {IMAGE:418495} |
| W89337 | 1.4 | 1.7 | 1.4 | IMAGE EST {IMAGE:418861} |
| W89466 | 1.4 | 1.7 | 1.2 | IMAGE EST {IMAGE:420591} |
| W48318 | 1.4 | −1.8 | 1.1 | IMAGE EST {IMAGE:355442} |
| AA476157 | 1.4 | 1.6 | 1.4 | IMAGE EST {IMAGE:876166} |
| AA498457 | 1.4 | 1.6 | 1.6 | Guanylate cyclase activator 2 (guanylin 2, intestinal, heatstable) {IMAGE:889440} |
| AA277407 | 1.4 | 1.7 | 1.6 | IMAGE EST {IMAGE:762256} |
| AA276003 | 1.4 | 1.9 | 1.3 | ESTs {IMAGE:775858} |
| AA212961 | 1.4 | 1.5 | 1.3 | IMAGE EST {IMAGE:676879} |
| AA215069 | 1.4 | 1.6 | 1.3 | IMAGE EST {IMAGE:651485} |
| AA108370 | 1.4 | −5.3 | 1.2 | Glutathione S-transferase, pi 2 {IMAGE:572002} |
| AA050964 | 1.4 | 1.5 | 1.1 | IMAGE EST {IMAGE:438580} |
| AA041709 | 1.4 | 1.4 | −1 | Phospholipase C, beta 3 {IMAGE:475397} |
| AA038737 | 1.4 | 1.6 | 1.2 | IMAGE EST {IMAGE:474184} |
| AA007769 | 1.4 | 2.3 | 1.3 | IMAGE EST {IMAGE:437674} |
| AA254100 | 1.4 | 1.6 | 1.3 | IMAGE EST {IMAGE:722336} |
| AA544895 | 1.4 | 1.7 | 1.4 | IMAGE EST {IMAGE:949246} |
| AA544963 | 1.4 | 1.5 | 1.3 | ESTs {IMAGE:948909} |
| AA051104 | 1.3 | 2.2 | −1 | IMAGE EST {IMAGE:438706} |
| AA116513 | 1.3 | 2.5 | −1.4 | Fatty acid synthase {IMAGE:576881} |
| AA290313 | 1.3 | 1.9 | 1.1 | ESTs {IMAGE:750782} |
| W98975 | 1.3 | 1.7 | 1.3 | ESTs {IMAGE:421145} |
| AA444640 | 1.3 | 1.5 | 1.5 | ESTs {IMAGE:831799} |
| AA267569 | 1.3 | 1.6 | 1.2 | ESTs {IMAGE:721421} |
| AA267721 | 1.3 | 1.5 | 1.5 | IMAGE EST {IMAGE:718372} |
| AA261454 | 1.3 | 1.5 | 1 | ESTs {IMAGE:720640} |
| AA244536 | 1.3 | 2.8 | 1.1 | ESTs {IMAGE:679244} |
| AA213048 | 1.3 | 1.8 | 1.3 | Hydroxysteroid 1 7-beta dehydrogenase 1 {IMAGE:677046} |
| AA125274 | 1.3 | 2.3 | −1.1 | IMAGE EST {IMAGE:574711} |
| AA051679 | 1.3 | 1.8 | 1.1 | ESTs, Highly similar to Similar to *S. cerevisiae* hypothetica protein N0330 [*H .sapiens*] {IMAGE:479759} |

B. Isolation of Full Length Mouse SGG Sequence

Figure 7A:
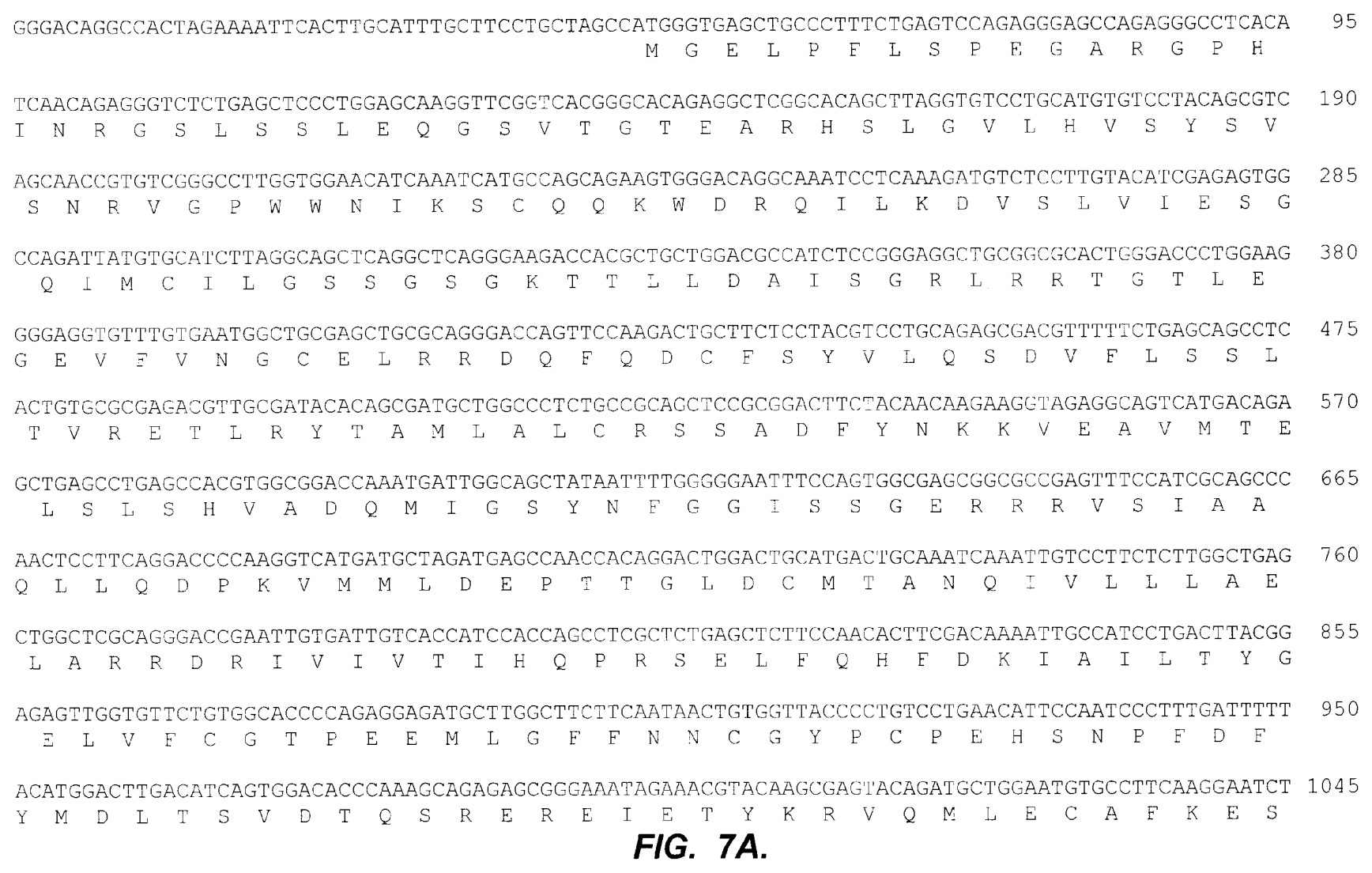

Two oligonucleotide primers were designed based on the sequence information from EST clone AA237916 (later found to represent murine SSG), which was found induced 2.4- and 2.5-fold in liver and intestine, respectively, of mice treated with LXR agonist Compound A (see, Table 2). These primers were then used to screen a mouse liver cDNA library (Origene Inc.). Multiple clones were identified and sequenced and one of these clones which we designated brown-like clone-1 (BL1; also called SSG) was used for subsequent analysis. Simultaneously, using the sequence information from BL1, searching the NCBI database (BLAST) resulted in the identification of an additional EST clone (AA656720) which gave rise to additional 3' DNA sequence. The full length amino acid and nucleotide sequences for murine SSG, or mSSG, are shown in FIG. 7 and in SEQ ID NOs:1 and 2.

C. Isolation of Human SGG Sequence

Using the mouse SSG sequence (BL1) the NCBI database was again searched and led to the identification of the human EST clone (T86384), sharing high sequence homology to the mouse BL1 clone. Sequence from the human BL1 EST was used to generate oligo primers which were used to screen the human liver cDNA library (Origene, Inc.). One of the clones generated from this screen contained approximately 100 additional base pairs 5' to the T86384.

The full length amino acid and nucleotide sequences for human SSG are shown in FIG. 8 and in SEQ ID NOs:3 and 4. A comparison of the human and mouse SSG amino acid sequences are shown in FIG. 9.

D. Determination of Map Position of Human, Mouse SGG Genes

The compiled human sequence (FIG. 8) was used to search NCBI EST database and resulted in the identification of EST T93792, which had been mapped to chromosome 2p21 between markers D2S177 and D2S119. The compiled mouse sequence described above was then used to identify a Unigene (Mm.100509) which had been previously mapped to mouse chromosome 17. This mouse chromosomal region is syntenic with human 2p21 (Locus Link, NCBI Database).

The map position of the human SSG was confirmed using the Stanford human TNG Radiation Hybrid Panel (Research Genetics). In this experiment, hSSG was localized between D2S117 and D2S119, consistent with the above-described mapping of the EST T93792. The results of this experiment are shown in FIG. 10, which shows three markers (SHGC-36672, SHGC-8189, and SHGC-699), each of which are located to 2p21, that were linked to the hSSG sequence with LOD scores of above 6. More information regarding these markers and the TNG Radiation Hybrid Panel can be obtained from the Stanford Human Genome Center (http://www-shgc.stanford.edu/).

Figure 1:
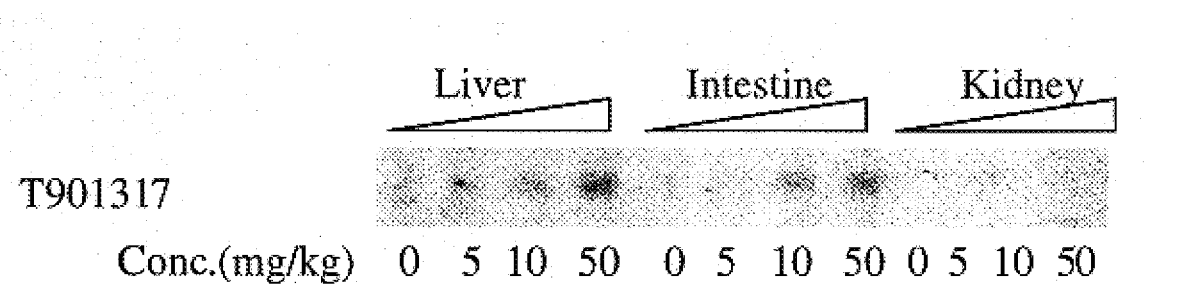
FIG. 1 shows a Northern blot that demonstrates that the LXR agonist Compound (Cpd.) A causes an increase in the level of SSG mRNA in the liver and the intestine.

E. Examination of SSG mRNA Expression in Liver, Intestine and Kidney of C57BL/6 Mice Treated with LXR Agonist Compound A Total RNA was prepared from untreated (control) and treated (0, 1, 5 and 50 mg/kg of LXRa agonist Compound A) C57BL/6 mouse liver, intestine and kidney. RNA was electrophoresed on 1.2% agarose/formaldehyde gels, transferred to nylon membrane (Ambion, Bright Star), hybridized to $^{32}$P-labeled murine SSG cDNA probe, washed and subjected to autoradiography. The results of this experiment, which demonstrate that SSG expression is induced in the liver and intestine by Compound A, are shown in FIG. 1.

F. Examination of SSG Expression Profile in the GI Tract

Figure 12:
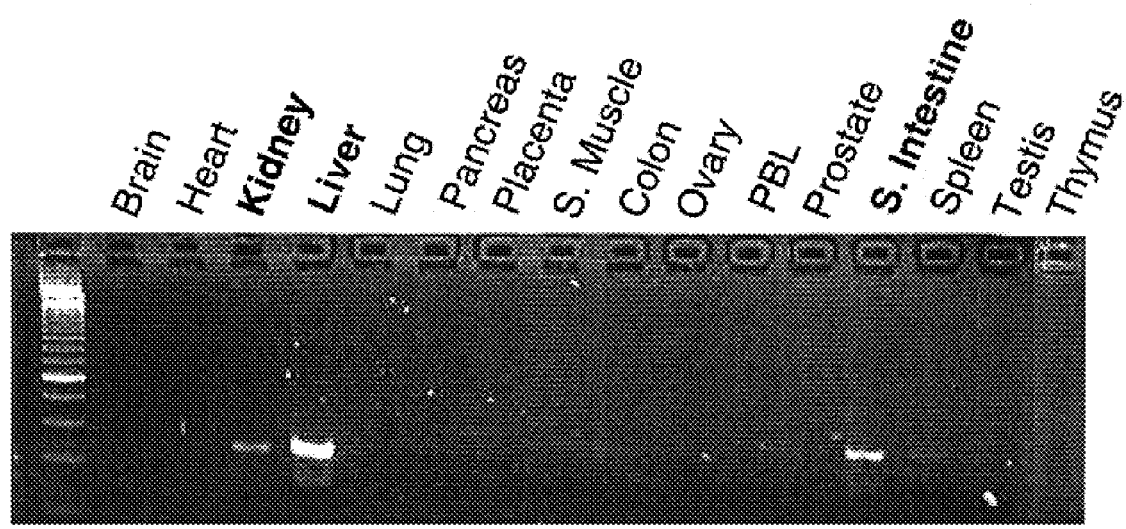
FIG. 12 shows that human SSG (or human ABCG5) is predominantly expressed in the liver and small intestine.
Figure 13:
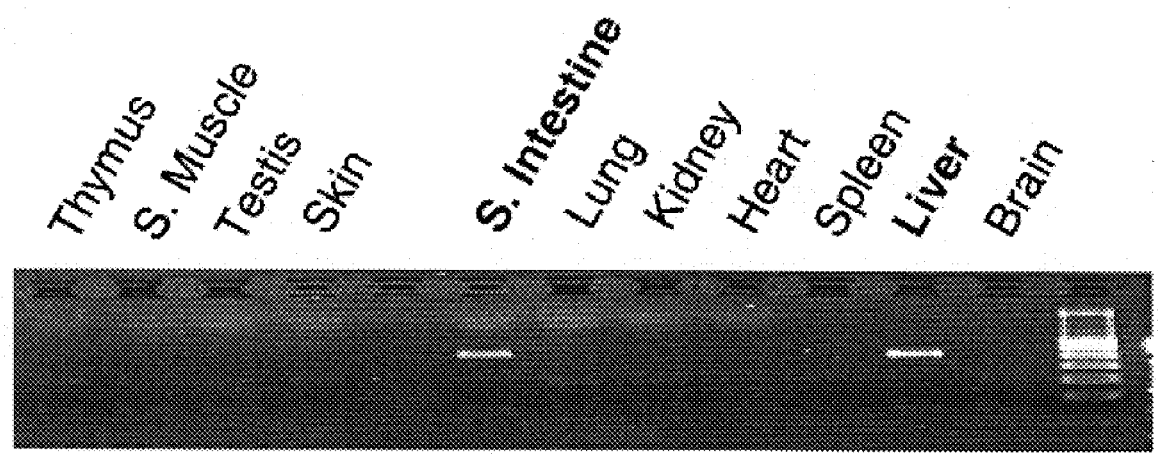
FIG. 13 shows that mouse SSG (or mouse ABCG5) is predominantly expressed in the liver and small intestine.

To determine where in the gastrointestinal tract SSG is expressed, human SSG mRNA expression was analyzed by PCR using a multiple tissue cDNA library and SSG-specific primers. As shown in FIGS. 11 and 12, significant expression was observed in this experiment in the liver, the jejunum, and ileum, and the duodenum. As the small intestine, comprising the duodenum, the jejunum, and the ileum, is the site of cholesterol absorption (in particular the jejunum), this result is consistent with the above-described role of SSG in cholesterol absorption. Similar expression data was found in mice. As shown in FIG. 13, mouse SSG (i.e., mouse ABCG5) is selectively expressed in the liver and small intestine.

G. Induction of ABC1 and ABC8 Expression by the LXR Agonists Compounds B and C

Figure 2:
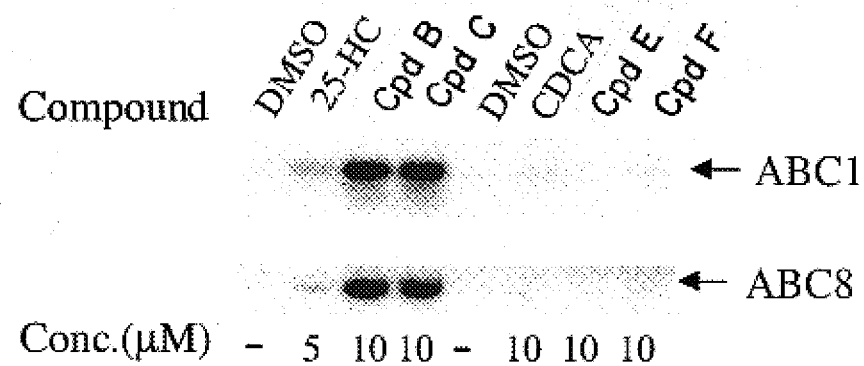
FIG. 2 shows a Northern blot demonstrating that the LXR agonists Compounds B and C produce an increase in the level of ABC1 and ABC8 mRNA.

Human Caco-2 cells were treated with Compounds B and C. Northern blot analysis was performed (essentially as described above) using human ABC1 and ABC8 cDNA probes. This experiment demonstrated that human ABC1 and ABC8 are induced in each of the tissues by Compounds B and C (FIG. 2).

H. Induction of ABC1 in Liver, Intestine and Kidney Of C57BL/6 Mice by LXRa Agonist Compound A This example demonstrates that the LXR agonist Compound A induces expression of the ABC transporter ABC1 in liver, intestine, and kidney of C57BL/6 mice.

Figure 3:
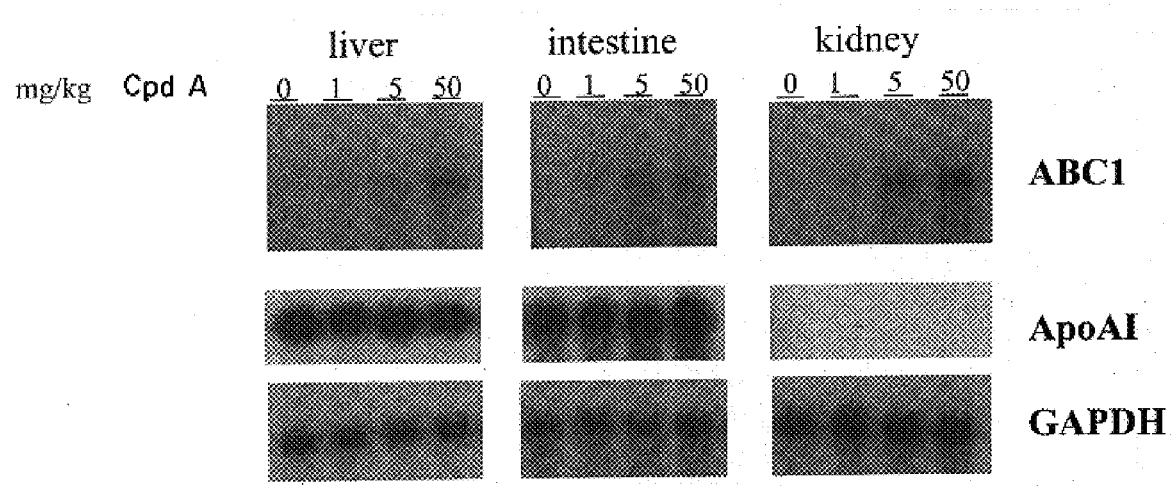
FIG. 3 shows a Northern blot demonstrating that the LXR agonist Compound A causes an increase in the level of expression of ABC1 in the liver, intestine, and kidney.

Total RNA was prepared from untreated (control) and treated (0, 1, 5 and 50 mg/kg of LXRa agonist Compound A) C57BL/6 mouse liver, intestine and kidney. RNA was electrophoresed on 1.2% agarose/formaldehyde gels, transferred to nylon membrane (Ambion, Bright Star), hybridized to $^{32}$P-labeled murine ABC-1, apolipoprotein AI, and GAPDH cDNA probes, washed and subjected to autoradiography. Dose dependent increases in ABC1 mRNA (FIG. 3) were detected in liver, intestine and kidney (of Compound A-treated mice) with no measurable difference seen in either apolipoprotein AI or GAPDH mRNA levels.

I. Compound A Stimulates Cholesterol Efflux From Caco-2 Cells

Figure 4:
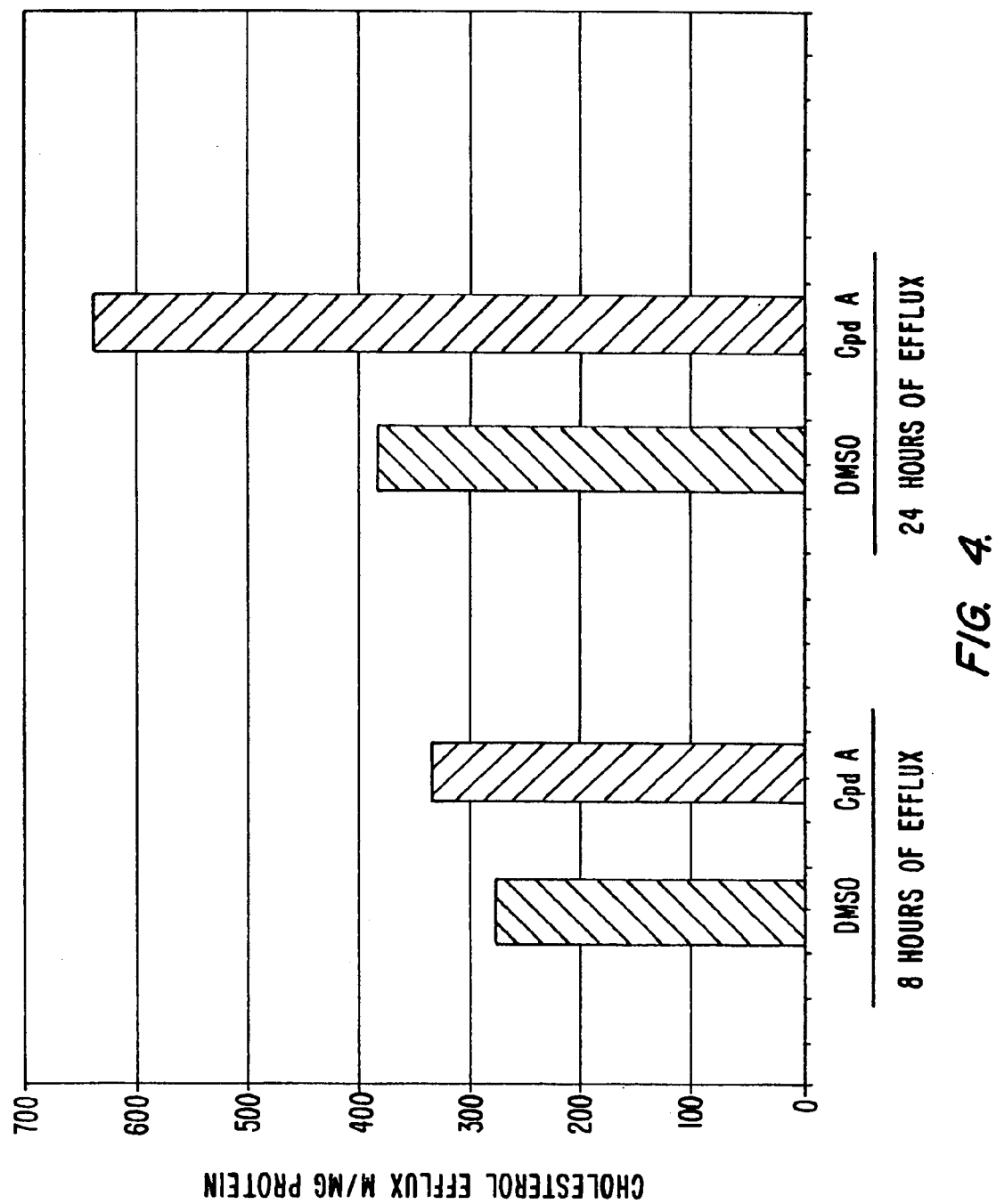
FIG. 4 demonstrates that the LXR agonist Compound A stimulates efflux of cholesterol from Caco-2 cells.

Caco2 cells (an adenocarcinoma cell line derived from human colon) were plated in 6 well plates at 50–60% confluence and allowed to adhere overnight in DMEM containing 10% FBS, non-essential amino acids, and Pen/Strep. On the second day, cells were labeled for 24 h with [$^3$H]-cholesterol (0.5 µCi/ml in DMEM and 1% BSA, Pen/Strep). Cells were washed (2×) with PBS and DMEM (1% BSA) with or without the addition of Compound A (1 µM final concentration). After 24 h treatment, cells were washed (2× with PBS) and efflux media was added containing purified apolipoprotein AI (10 ug/ml). Cells and media were harvested at 8 and 24 hour time points. Cells were washed 3× with PBS, and lysed with 300 µl of 0.5 M NaOH. Radioactivity in media and cell lysates were scintillation counted and normalized to cell protein (using BioRad Lowry Kit). Efflux data shown in is presented as CPM (media)/mg cell protein (FIG. 4).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. An isolated nucleic acid encoding an ATP-binding cassette (ABC) family sterol transporter polypeptide, said polypeptide comprising an amino acid sequence that is at least 95% identical to the full-length of an amino acid sequence as set forth in SEQ ID NO:3, wherein said nucleic acid hybridizes under stringent hybridization conditions comprising 50% formamide, 5×SSC, 1% SDS at 65° C. and wash conditions of 0.2×SSC, 0.1% SDS at 65° C. to a nucleic acid comprising a nucleotide sequence as set forth in SEQ ID NO:4, and where said amino acid sequence comprises an ATP-binding cassette (ABC) family sterol transporter.

2. The nucleic acid of claim 1, wherein said polypeptide specifically binds to monoclonal antibodies generated against a polypeptide that comprises an amino acid sequence as set forth in SEQ ID NO:3.

3. The nucleic acid of claim 1, wherein said polypeptide comprises an amino acid sequence as set forth in SEQ ID NO:3.

4. The nucleic acid of claim 1, wherein said polypeptide forms a dimer with a second ABC polypeptide, and wherein said dimer has sterol transport activity.

5. The nucleic acid of claim 4, wherein said dimer is a heterodimer.

6. The nucleic acid of claim 4, wherein said sterol is cholesterol.

7. The nucleic acid of claim 5, wherein said second ABC polypeptide is ATP-Binding Cassette 8 (ABC8).

8. The nucleic acid of claim 1, wherein said nucleic acid comprises a nucleotide sequence as set forth in SEQ ID NO:4.

9. The nucleic acid of claim 1, wherein said nucleic acid is form a mouse or a human.

10. The nucleic acid of claim 1, wherein said nucleic acid is expressed in the intestine or in the liver in the presence of a liver X receptor (LXR) agonist.

11. The nucleic acid of claim 1, wherein said nucleic acid is expressed in a tissue selected from the group consisting of liver, jejunum, ileum, and duodenum.

12. An expression cassette comprising the nucleic acid of claim 1 operably linked to a promoter.

13. An isolated cell tranformed with the expression cassette of claim 12.

14. A method of making an ABC family sterol transporter polypeptide, the method comprising:

(i) introducing a nucleic acid of claim 1 into a host cell or cellular extract; and (ii) incubating said host cell or cellular extract under conditions such that said ABC family sterol transporter polypeptide is expressed in the host cell or cellular extract.

15. The method of claim 14, further comprising recovering the SSG polypeptide from the host cell or cellular extract.

16. An isolated nucleic acid encoding an ATP-binding cassette (ABC) family sterol transporter polypeptide, said polypeptide comprising an amino acid sequence that is at least 95% identical to the full-length of an amino acid sequence as set forth in SEQ ID NO:3, and wherein said amino acid sequence comprises an ATP-binding cassette (ABC) family sterol transporter.

17. An isolated nucleic acid encoding an ATP-binding cassette (ABC) family sterol transporter polypeptide, wherein said nucleic acid comprises a nucleotide sequence at least 95% identical to the full-length of a sequence as set forth in SEQ ID NO:4.

18. An isolated nucleic acid encoding an ATP-binding cassette (ABC) family sterol transporter polypeptide, wherein said polypeptide comprises an amino acid sequence as set forth in SEQ ID NO:3.

19. An isolated nucleic acid encoding an ATP-binding cassette (ABC) family sterol transporter polypeptide, wherein said nucleic acid comprises a nucleotide sequence as set forth in SEQ ID NO:4.

* * * * *

UNITED STATES PATENT AND TRADEMARK OFFICE
CERTIFICATE OF CORRECTION

PATENT NO. : 7,033,810 B2
APPLICATION NO. : 09/837992
DATED : April 25, 2006
INVENTOR(S) : Tian et al.

It is certified that error appears in the above-identified patent and that said Letters Patent is hereby corrected as shown below:

Col. 78, in Claim 15, line 2, the term reading "SSG" should read --ABC family sterol transporter--.

Signed and Sealed this

Eighth Day of August, 2006

JON W. DUDAS
*Director of the United States Patent and Trademark Office*

SEQUENCE LISTING

<160> NUMBER OF SEQ ID NOS: 45

<210> SEQ ID NO 1
<211> LENGTH: 652
<212> TYPE: PRT
<213> ORGANISM: Mus musculus
<220> FEATURE:
<223> OTHER INFORMATION: mouse sitosterolemia susceptibility gene (SSG)
      amino acid sequence

<400> SEQUENCE: 1

Met Gly Glu Leu Pro Phe Leu Ser Pro Glu Gly Ala Arg Gly Pro His
 1               5                  10                  15

Ile Asn Arg Gly Ser Leu Ser Ser Leu Glu Gln Gly Ser Val Thr Gly
                20                  25                  30

Thr Glu Ala Arg His Ser Leu Gly Val Leu His Val Ser Tyr Ser Val
            35                  40                  45

Ser Asn Arg Val Gly Pro Trp Trp Asn Ile Lys Ser Cys Gln Gln Lys
        50                  55                  60

Trp Asp Arg Gln Ile Leu Lys Asp Val Ser Leu Tyr Ile Glu Ser Gly
 65                  70                  75                  80

Gln Ile Met Cys Ile Leu Gly Ser Ser Gly Ser Gly Lys Thr Thr Leu
                85                  90                  95

Leu Asp Ala Ile Ser Gly Arg Leu Arg Arg Thr Gly Thr Leu Glu Gly
            100                 105                 110

Glu Val Phe Val Asn Gly Cys Glu Leu Arg Arg Asp Gln Phe Gln Asp
        115                 120                 125

Cys Phe Ser Tyr Val Leu Gln Ser Asp Val Phe Leu Ser Ser Leu Thr
    130                 135                 140

Val Arg Glu Thr Leu Arg Tyr Thr Ala Met Leu Ala Leu Cys Arg Ser
145                 150                 155                 160

Ser Ala Asp Phe Tyr Asn Lys Lys Val Glu Ala Val Met Thr Glu Leu
                165                 170                 175

Ser Leu Ser His Val Ala Asp Gln Met Ile Gly Ser Tyr Asn Phe Gly
            180                 185                 190

Gly Ile Ser Ser Gly Glu Arg Arg Val Ser Ile Ala Ala Gln Leu
        195                 200                 205

Leu Gln Asp Pro Lys Val Met Met Leu Asp Glu Pro Thr Thr Gly Leu
    210                 215                 220

Asp Cys Met Thr Ala Asn Gln Ile Val Leu Leu Ala Glu Leu Ala
225                 230                 235                 240

Arg Arg Asp Arg Ile Val Ile Val Thr Ile His Gln Pro Arg Ser Glu
                245                 250                 255

Leu Phe Gln His Phe Asp Lys Ile Ala Ile Leu Thr Tyr Gly Glu Leu
            260                 265                 270

Val Phe Cys Gly Thr Pro Glu Glu Met Leu Gly Phe Asn Asn Cys
        275                 280                 285

Gly Tyr Pro Cys Pro Glu His Ser Asn Pro Phe Asp Phe Tyr Met Asp
    290                 295                 300

Leu Thr Ser Val Asp Thr Gln Ser Arg Glu Arg Glu Ile Glu Thr Tyr
305                 310                 315                 320

Lys Arg Val Gln Met Leu Glu Cys Ala Phe Lys Glu Ser Asp Ile Tyr
                325                 330                 335

His Lys Ile Leu Glu Asn Ile Glu Arg Ala Arg Tyr Leu Lys Thr Leu

-continued

```
            340                 345                 350
Pro Met Val Pro Phe Lys Thr Lys Asp Pro Pro Gly Met Phe Gly Lys
            355                 360                 365
Leu Gly Val Leu Leu Arg Arg Val Thr Arg Asn Leu Met Arg Asn Lys
370                 375                 380
Gln Ala Val Ile Met Arg Leu Val Gln Asn Leu Ile Met Gly Leu Phe
385                 390                 395                 400
Leu Ile Phe Tyr Leu Leu Arg Val Gln Asn Asn Thr Leu Lys Gly Ala
                405                 410                 415
Val Gln Asp Arg Val Gly Leu Leu Tyr Gln Leu Val Gly Ala Thr Pro
            420                 425                 430
Tyr Thr Gly Met Leu Asn Ala Val Asn Leu Phe Pro Met Leu Arg Ala
            435                 440                 445
Val Ser Asp Gln Glu Ser Gln Asp Gly Leu Tyr His Lys Trp Gln Met
        450                 455                 460
Leu Leu Ala Tyr Val Leu His Val Leu Pro Phe Ser Val Ile Ala Thr
465                 470                 475                 480
Val Ile Phe Ser Ser Val Cys Tyr Trp Thr Leu Gly Leu Tyr Pro Glu
                485                 490                 495
Val Ala Arg Phe Gly Tyr Phe Ser Ala Ala Leu Leu Ala Pro His Leu
            500                 505                 510
Ile Gly Glu Phe Leu Thr Leu Val Leu Leu Gly Ile Val Gln Asn Pro
            515                 520                 525
Asn Ile Val Asn Ser Ile Val Ala Leu Leu Ser Ile Ser Gly Leu Leu
        530                 535                 540
Ile Gly Ser Gly Phe Ile Arg Asn Ile Gln Glu Met Pro Ile Pro Leu
545                 550                 555                 560
Lys Ile Leu Gly Tyr Phe Thr Phe Gln Lys Tyr Cys Cys Glu Ile Leu
                565                 570                 575
Val Val Asn Glu Phe Tyr Gly Leu Asn Phe Thr Cys Gly Gly Ser Asn
            580                 585                 590
Thr Ser Met Leu Asn His Pro Met Cys Ala Ile Thr Gln Gly Val Gln
            595                 600                 605
Phe Ile Glu Lys Thr Cys Pro Gly Ala Thr Ser Arg Phe Thr Ala Asn
        610                 615                 620
Phe Leu Ile Leu Tyr Gly Phe Ile Pro Ala Leu Val Ile Leu Gly Ile
625                 630                 635                 640
Val Ile Phe Lys Val Arg Asp Tyr Leu Ile Ser Arg
                645                 650
```

<210> SEQ ID NO 2
<211> LENGTH: 2258
<212> TYPE: DNA
<213> ORGANISM: Mus musculus
<220> FEATURE:
<223> OTHER INFORMATION: mouse sitosterolemia susceptibility gene (SSG)
<221> NAME/KEY: CDS
<222> LOCATION: (47)..(2005)
<223> OTHER INFORMATION: mouse sitosterolemia susceptibility gene (SSG)
      protein

<400> SEQUENCE: 2
gggacaggcc actagaaaat tcacttgcat ttgcttcctg ctagccatgg gtgagctgcc        60
ctttctgagt ccagagggag ccagagggcc tcacatcaac agagggtctc tgagctccct       120
ggagcaaggt tcggtcacgg gcacagaggc tcggcacagc ttaggtgtcc tgcatgtgtc       180

```
ctacagcgtc agcaaccgtg tcgggccttg gtggaacatc aaatcatgcc agcagaagtg      240
ggacaggcaa atcctcaaag atgtctcctt gtacatcgag agtggccaga ttatgtgcat      300
cttaggcagc tcaggctcag ggaagaccac gctgctggac gccatctccg ggaggctgcg      360
gcgcactggg accctggaag gggaggtgtt tgtgaatggc tgcgagctgc gcagggacca      420
gttccaagac tgcttctcct acgtcctgca gagcgacgtt tttctgagca gcctcactgt      480
gcgcgagacg ttgcgataca cagcgatgct ggccctctgc cgcagctccg cggacttcta      540
caacaagaag gtagaggcag tcatgacaga gctgagcctg agccacgtgg cggaccaaat      600
gattggcagc tataattttg ggggaatttc cagtggcgag cggcgccgag tttccatcgc      660
agcccaactc cttcaggacc ccaaggtcat gatgctagat gagccaacca caggactgga      720
ctgcatgact gcaaatcaaa ttgtccttct cttggctgag ctggctcgca gggaccgaat      780
tgtgattgtc accatccacc agcctcgctc tgagctcttc caacacttcg acaaaattgc      840
catcctgact tacggagagt tggtgttctg tggcacccca gaggagatgc ttggcttctt      900
caataactgt ggttacccct gtcctgaaca ttccaatccc tttgattttt acatggactt      960
gacatcagtg gacacccaaa gcagagagcg ggaaatagaa acgtacaagc gagtacagat     1020
gctggaatgt gccttcaagg aatctgacat ctatcacaaa attctggaga acattgaaag     1080
agcacgatac ctgaaaacct tacccatggt tcctttcaaa acaaaagatc ctcctgggat     1140
gttcggcaag cttggtgtcc tgctgaggcg agtaacaaga aacttaatga ggaataagca     1200
ggcagtgatt atgcgtctcg ttcagaatct gatcatgggc ctcttcctca ttttctacct     1260
tctccgcgtc cagaacaaca cgctaaaggg cgctgtgcag gaccgcgtgg ggctgctcta     1320
tcagcttgtg ggtgccaccc catacaccgg catgctcaat gctgtgaatc tgtttcccat     1380
gctgagagcc gtcagcgacc aggagagtca ggatggcctg tatcataagt ggcagatgct     1440
gctcgcctac gtgctacacg tcctccccctt cagcgtcatc gccacggtca ttttcagcag     1500
tgtgtgttat tggactctgg gcttgtatcc tgaagttgcc agatttggat atttctctgc     1560
tgctcttttg gcccctcact taattggaga atttctaaca cttgtgctgc ttggtatagt     1620
ccaaaaccct aatattgtca acagtatagt ggctctgctc agcatctctg gctgcttat      1680 tggatctgga tttatcagaa acatacaaga aatgcccatt cctttaaaaa tcctgggtta     1740
ttttacattc caaaaatact gttgtgagat tctcgtggtc aatgagtttt acggcctgaa     1800
cttcacttgt ggtggatcca acacctctat gctaaatcac ccgatgtgcg ccatcaccca     1860 agggtccag ttcatcgaga aaacctgccc aggtgctaca tccagattca cggcaaactt      1920
cctcatctta tatgggttta tcccagctct ggtcatccta ggaatagtga tttttaaagt     1980
cagggactac ctgattagca gatagttaag atgacaggca ggaaagggtt aatgggcagg     2040
cacgcccact gtggagcaca gagaagtact gtcttcaacc atcaggattc catctgcgac     2100
ccttgtgtct gacccttgtg tctatccgga gcccaagggc aacgagaac tcacagccct      2160 ctgctattcc agcttgtggg gcaatgtggt gcttggacat tgtgactgaa ctggtccaat     2220
aatgtaaata ataataattc ataaacctac aggacatt                             2258
```

<210> SEQ ID NO 3
<211> LENGTH: 651
<212> TYPE: PRT
<213> ORGANISM: Homo sapiens
<220> FEATURE:
<223> OTHER INFORMATION: human sitosterolemia susceptibility gene (SSG)
      amino acid sequence

<400> SEQUENCE: 3

-continued

```
Met Gly Asp Leu Ser Ser Leu Thr Pro Gly Gly Ser Met Gly Leu Gln
 1               5                  10                  15

Val Asn Arg Gly Ser Gln Ser Ser Leu Glu Gly Ala Pro Ala Thr Ala
             20                  25                  30

Pro Glu Pro His Ser Leu Gly Ile Leu His Ala Ser Tyr Ser Val Ser
             35                  40                  45

His Arg Val Arg Pro Trp Trp Asp Ile Thr Ser Cys Arg Gln Gln Trp
 50                  55                  60

Thr Arg Gln Ile Leu Lys Asp Val Ser Leu Tyr Val Glu Ser Gly Gln
 65                  70                  75                  80

Ile Met Cys Ile Leu Gly Ser Ser Gly Ser Gly Lys Thr Thr Leu Leu
                 85                  90                  95

Asp Ala Met Ser Gly Arg Leu Gly Arg Ala Gly Thr Phe Leu Gly Glu
             100                 105                 110

Val Tyr Val Asn Gly Arg Ala Leu Arg Arg Glu Gln Phe Gln Asp Cys
             115                 120                 125

Phe Ser Tyr Val Leu Gln Ser Asp Thr Leu Leu Ser Ser Leu Thr Val
 130                 135                 140

Arg Glu Thr Leu His Tyr Thr Ala Leu Leu Ala Ile Arg Arg Gly Asn
145                 150                 155                 160

Pro Gly Ser Phe Gln Lys Lys Val Glu Ala Val Met Ala Glu Leu Ser
                 165                 170                 175

Leu Ser His Val Ala Asp Arg Leu Ile Gly Asn Tyr Ser Leu Gly Gly
             180                 185                 190

Ile Ser Thr Gly Glu Arg Arg Arg Val Ser Ile Ala Ala Gln Leu Leu
             195                 200                 205

Gln Asp Pro Lys Val Met Leu Phe Asp Glu Pro Thr Thr Gly Leu Asp
             210                 215                 220

Cys Met Thr Ala Asn Gln Ile Val Val Leu Val Glu Leu Ala Arg
225                 230                 235                 240

Arg Asn Arg Ile Val Val Leu Thr Ile His Gln Pro Arg Ser Glu Leu
                 245                 250                 255

Phe Gln Leu Phe Asp Lys Ile Ala Ile Leu Ser Phe Gly Glu Leu Ile
             260                 265                 270

Phe Cys Gly Thr Pro Ala Glu Met Leu Asp Phe Phe Asn Asp Cys Gly
             275                 280                 285

Tyr Pro Cys Pro Glu His Ser Asn Pro Phe Asp Phe Tyr Met Asp Leu
             290                 295                 300

Thr Ser Val Asp Thr Gln Ser Lys Glu Arg Glu Ile Glu Thr Ser Lys
305                 310                 315                 320

Arg Val Gln Met Ile Glu Ser Ala Tyr Lys Ser Ala Ile Cys His
                 325                 330                 335

Lys Thr Leu Lys Asn Ile Glu Arg Met Lys His Leu Lys Thr Leu Pro
                 340                 345                 350

Met Val Pro Phe Lys Thr Lys Asp Ser Pro Gly Val Phe Ser Lys Leu
             355                 360                 365

Gly Val Leu Leu Arg Arg Val Thr Arg Asn Leu Val Arg Asn Lys Leu
 370                 375                 380

Ala Val Ile Thr Arg Leu Leu Gln Asn Leu Ile Met Gly Leu Phe Leu
385                 390                 395                 400

Leu Phe Phe Val Leu Arg Val Arg Ser Asn Val Leu Lys Gly Ala Ile
                 405                 410                 415
```

```
Gln Asp Arg Val Gly Leu Leu Tyr Gln Phe Val Gly Ala Thr Pro Tyr
            420                 425                 430
Thr Gly Met Leu Asn Ala Val Asn Leu Phe Pro Val Leu Arg Ala Val
        435                 440                 445
Ser Asp Gln Glu Ser Gln Asp Gly Leu Tyr Gln Lys Trp Gln Met Met
    450                 455                 460
Leu Ala Tyr Ala Leu His Val Leu Pro Phe Ser Val Val Ala Thr Met
465                 470                 475                 480
Ile Phe Ser Ser Val Cys Tyr Trp Thr Leu Gly Leu His Pro Glu Val
                485                 490                 495
Ala Arg Phe Gly Tyr Phe Ser Ala Ala Leu Leu Ala Pro His Leu Ile
            500                 505                 510
Gly Glu Phe Leu Thr Leu Val Leu Leu Gly Ile Val Gln Asn Pro Asn
        515                 520                 525
Ile Val Asn Ser Val Val Ala Leu Leu Ser Ile Ala Gly Val Leu Val
    530                 535                 540
Gly Ser Gly Phe Leu Arg Asn Ile Gln Glu Met Pro Ile Pro Phe Lys
545                 550                 555                 560
Ile Ile Ser Tyr Phe Thr Phe Gln Lys Tyr Cys Ser Glu Ile Leu Val
                565                 570                 575
Val Asn Glu Phe Tyr Gly Leu Asn Phe Thr Cys Gly Ser Ser Asn Val
            580                 585                 590
Ser Val Thr Thr Asn Pro Met Cys Ala Phe Thr Gln Gly Ile Gln Phe
        595                 600                 605
Ile Glu Lys Thr Cys Pro Gly Ala Thr Ser Arg Phe Thr Met Asn Phe
    610                 615                 620
Leu Ile Leu Tyr Ser Phe Ile Pro Ala Leu Val Ile Leu Gly Ile Val
625                 630                 635                 640
Val Phe Lys Ile Arg Asp His Leu Ile Ser Arg
                645                 650

<210> SEQ ID NO 4
<211> LENGTH: 2340
<212> TYPE: DNA
<213> ORGANISM: Homo sapiens
<220> FEATURE:
<223> OTHER INFORMATION: human sitosterolemia gene (SSG)
<221> NAME/KEY: CDS
<222> LOCATION: (107)..(2062)
<223> OTHER INFORMATION: human sitosterolemia susceptibility gene (SSG)
      protein

<400> SEQUENCE: 4
gtcaggtgga gcaggcaggg cagtctgcca cgggctcccc aactgaagcc actctgggga      60
gggtccggcc accagaaaat tgcccagct  ttgctgcctg ttggccatgg gtgacctctc     120
atctttgacc cccggagggt ccatgggtct ccaagtaaac agaggctccc agagctccct    180
ggagggggct cctgccaccg ccccggagcc tcacagcctg gcatcctcc  atgcctccta    240 cagcgtcagc caccgcgtga ggccctggtg gacatcaca  tcttgccggc agcagtggac    300
caggcagatc ctcaaagatg tctccttgta cgtggagagc gggcagatca tgtgcatcct    360
aggaagctca ggctccggga aaaccacgct gctggacgcc atgtccggga ggctggggcg    420
cgcggggacc ttcctggggg aggtgtatgt gaacggccgg gcgctgcgcc gggagcagtt    480
ccaggactgc ttctcctacg tcctgcagag cgacaccctg ctgagcagcc tcaccgtgcg    540
cgagacgctg cactacaccg cgctgctggc catccgccgc ggcaatcccg gctccttcca    600
```

```
gaagaaggtg gaggccgtca tggcagagct gagtctgagc catgtggcag accgactgat      660
tggcaactac agcttggggg gcatttccac gggtgagcgg cgccgggtct ccatcgcagc      720
ccagctgctc caggatccta aggtcatgct gtttgatgag ccaaccacag gcctggactg      780
catgactgct aatcagattg tcgtcctcct ggtggaactg gctcgcagga accgaattgt      840
ggttctcacc attcaccagc cccgttctga gcttttcag ctctttgaca aaattgccat       900
cctgagcttc ggagagctga ttttctgtgg cacgccagcg gaaatgcttg atttcttcaa      960
tgactgcggt taccttgtc ctgaacattc aaacccttt gacttctata tggacctgac       1020
gtcagtggat acccaaagca aggaacggga atagaaacc tccaagagag tccagatgat      1080
agaatctgcc tacaagaaat cagcaatttg tcataaaact ttgaagaata ttgaaagaat      1140
gaaacacctg aaaacgttac caatggttcc tttcaaaacc aaagattctc ctggagtttt     1200
ctctaaactg ggtgttctcc tgaggagagt gacaagaaac ttggtgagaa ataagctggc     1260
agtgattacg cgtctccttc agaatctgat catgggtttg ttcctccttt cttcgttct     1320
gcgggtccga agcaatgtgc taaagggtgc tatccaggac cgcgtaggtc cctttacca     1380
gtttgtgggc gccaccccgt acacaggcat gctgaacgct gtgaatctgt ttcccgtgct    1440
gcgagctgtc agcgaccagg agagtcagga cggcctctac cagaagtggc agatgatgct   1500
ggcctatgca ctgcacgtcc tccccttcag cgttgttgcc accatgattt tcagcagtgt   1560
gtgctactgg acgctgggct acatcctga ggttgcccga tttggatatt tttctgctgc    1620
tctcttggcc ccccacttaa ttggtgaatt tctaactctt gtgctacttg gtatcgtcca    1680
aaatccaaat atagtcaaca gtgtagtggc tctgctgtcc attgcggggg tgcttgttgg   1740
atctggattc ctcagaaaca tacaagaaat gcccattcct tttaaaatca tcagttattt   1800
tacattccaa aaatattgca gtgagattct tgtagtcaat gagttctacg gactgaattt   1860
cacttgtggc agctcaaatg tttctgtgac aactaatcca atgtgtgcct tcactcaagg   1920
aattcaattc attgagaaaa cctgcccagg tgcaacatct agattcacaa tgaactttct   1980
gattttgtat tcatttattc cagctcttgt catcctagga atagttgttt tcaaaataag    2040
ggatcatctc attagcaggt agtgaaagcc atggctggga aaatggaagt gaagctgccg   2100
actgtgcatg actgctctga acgtctgaaa tgagagtgcc atgtatttct ttcttgacag    2160
gacatctcaa gtcttttaac cattaagact ccatttgtgc ctcttggatc caagcaggcc   2220
ttgaatgcaa tggaagtggt ttatagtccc ttgctcttac aacttgcagg acatgtggt    2280
tatttggaaa ttgtgactga gcggacccaa gaatgtaaat aatattcata aacctatggg   2340
<210> SEQ ID NO 5
<211> LENGTH: 18
<212> TYPE: PRT
<213> ORGANISM: Homo sapiens
<220> FEATURE:
<223> OTHER INFORMATION: SSG signature sequence 1

<400> SEQUENCE: 5

Ala Ala Leu Leu Ala Pro His Leu Ile Gly Glu Phe Leu Thr Leu Val
 1               5                  10                  15

Leu Leu

<210> SEQ ID NO 6
<211> LENGTH: 11
<212> TYPE: PRT
<213> ORGANISM: Homo sapiens
<220> FEATURE:
<223> OTHER INFORMATION: SSG signature sequence 2
```

```
<400> SEQUENCE: 6

Phe Ile Pro Ala Leu Val Ile Leu Gly Ile Val
 1               5                   10

<210> SEQ ID NO 7
<211> LENGTH: 249
<212> TYPE: DNA
<213> ORGANISM: Homo sapiens
<220> FEATURE:
<223> OTHER INFORMATION: exon 1 of hSSG

<400> SEQUENCE: 7
gtcaggtgga gcaggcaggg cagtctgcca cgggctcccc aactgaagcc actctgggga      60
gggtccggcc accagaaaat tgcccagct ttgctgcctg ttggccatgg gtgacctctc      120
atctttgacc cccggagggt ccatgggtct ccaagtaaac agaggctccc agagctccct    180
ggagggggct cctgccaccg ccccggagcc tcacagcctg ggcatcctcc atgcctccta    240
cagcgtcag                                                             249

<210> SEQ ID NO 8
<211> LENGTH: 122
<212> TYPE: DNA
<213> ORGANISM: Homo sapiens
<220> FEATURE:
<223> OTHER INFORMATION: exon 2 of hSSG

<400> SEQUENCE: 8
ccaccgcgtg aggccctggt gggacatcac atcttgccgg cagcagtgga ccaggcagat     60
cctcaaagat gtctccttgt acgtggagag cgggcagatc atgtgcatcc taggaagctc    120
ag                                                                    122

<210> SEQ ID NO 9
<211> LENGTH: 137
<212> TYPE: DNA
<213> ORGANISM: Homo sapiens
<220> FEATURE:
<223> OTHER INFORMATION: exon 3 of hSSG

<400> SEQUENCE: 9
gctccgggaa aaccacgctg ctggacgcca tgtccgggag gctggggcgc gcggggacct     60
tcctggggga ggtgtatgtg aacggccggg cgctgcgccg ggagcagttc caggactgct    120
tctcctacgt cctgcag                                                    137

<210> SEQ ID NO 10
<211> LENGTH: 103
<212> TYPE: DNA
<213> ORGANISM: Homo sapiens
<220> FEATURE:
<223> OTHER INFORMATION: exon 4 of hSSG

<400> SEQUENCE: 10
agcgacaccc tgctgagcag cctcaccgtg cgcgagacgc tgcactacac cgcgctgctg     60
gccatccgcc gcggcaatcc cggctccttc agaagaaagg tgg                       103

<210> SEQ ID NO 11
<211> LENGTH: 129
<212> TYPE: DNA
<213> ORGANISM: Homo sapiens
<220> FEATURE:
<223> OTHER INFORMATION: exon 5 of hSSG
```

```
<400> SEQUENCE: 11
aggccgtcat ggcagagctg agtctgagcc atgtggcaga ccgactgatt ggcaactaca      60
gcttgggggg catttccacg ggtgagcggc gccgggtctc catcgcagcc cagctgctcc     120
aggatccta                                                             129

<210> SEQ ID NO 12
<211> LENGTH: 140
<212> TYPE: DNA
<213> ORGANISM: Homo sapiens
<220> FEATURE:
<223> OTHER INFORMATION: exon 6 of hSSG

<400> SEQUENCE: 12
aggtcatgct gtttgatgag ccaaccacag gcctggactg catgactgct aatcagattg      60
tcgtcctcct ggtggaactg gctcgcagga accgaattgt ggttctcacc attcaccagc    120
cccgttctga gcttttcag                                                  140

<210> SEQ ID NO 13
<211> LENGTH: 130
<212> TYPE: DNA
<213> ORGANISM: Homo sapiens
<220> FEATURE:
<223> OTHER INFORMATION: exon 7 of hSSG

<400> SEQUENCE: 13
ctctttgaca aaattgccat cctgagcttc ggagagctga ttttctgtgg cacgccagcg      60
gaaatgcttg atttcttcaa tgactgcggt taccttgtc ctgaacattc aaacccttt      120 gacttctata                                                            130

<210> SEQ ID NO 14
<211> LENGTH: 214
<212> TYPE: DNA
<213> ORGANISM: Homo sapiens
<220> FEATURE:
<223> OTHER INFORMATION: exon 8 of hSSG

<400> SEQUENCE: 14
tggacctgac gtcagtggat acccaaagca aggaacggga aatagaaacc tccaagagag      60
tccagatgat agaatctgcc tacaagaaat cagcaatttg tcataaaact ttgaagaata    120
ttgaaagaat gaaacacctg aaaacgttac caatggttcc tttcaaaacc aaagattctc    180
ctggagtttt ctctaaactg ggtgttctcc tgag                                 214

<210> SEQ ID NO 15
<211> LENGTH: 206
<212> TYPE: DNA
<213> ORGANISM: Homo sapiens
<220> FEATURE:
<223> OTHER INFORMATION: exon 9 of hSSG

<400> SEQUENCE: 15
gagagtgaca agaaacttgg tgagaaataa gctggcagtg attacgcgtc tccttcagaa      60
tctgatcatg ggtttgttcc tccttttctt cgttctgcgg gtccgaagca atgtgctaaa    120
gggtgctatc caggaccgcg taggtctcct ttaccagttt gtgggcgcca ccccgtacac    180
aggcatgctg aacgctgtga atctgt                                          206

<210> SEQ ID NO 16
<211> LENGTH: 139
```

```
<212> TYPE: DNA
<213> ORGANISM: Homo sapiens
<220> FEATURE:
<223> OTHER INFORMATION: exon 10 of hSSG

<400> SEQUENCE: 16
ttcccgtgct gcgagctgtc agcgaccagg agagtcagga cggcctctac cagaagtggc      60
agatgatgct ggcctatgca ctgcacgtcc tccccttcag cgttgttgcc accatgattt     120
tcagcagtgt gtgctactg                                                  139

<210> SEQ ID NO 17
<211> LENGTH: 186
<212> TYPE: DNA
<213> ORGANISM: Homo sapiens
<220> FEATURE:
<223> OTHER INFORMATION: exon 11 of hSSG

<400> SEQUENCE: 17
gacgctgggc ttacatcctg aggttgcccg atttggatat ttttctgctg ctctcttggc      60
cccccactta attggtgaat ttctaactct tgtgctactt ggtatcgtcc aaaatccaaa     120
tatagtcaac agtgtagtgg ctctgctgtc cattgcgggg gtgcttgttg gatctggatt     180
cctcag                                                                186

<210> SEQ ID NO 18
<211> LENGTH: 113
<212> TYPE: DNA
<213> ORGANISM: Homo sapiens
<220> FEATURE:
<223> OTHER INFORMATION: exon 12 of hSSG

<400> SEQUENCE: 18
aaacatacaa gaaatgccca ttccttttaa aatcatcagt tattttacat tccaaaaata      60
ttgcagtgag attcttgtag tcaatgagtt ctacggactg aatttcactt gtg            113

<210> SEQ ID NO 19
<211> LENGTH: 472
<212> TYPE: DNA
<213> ORGANISM: Homo sapiens
<220> FEATURE:
<223> OTHER INFORMATION: exon 13 of hSSG

<400> SEQUENCE: 19
gcagctcaaa tgtttctgtg acaactaatc caatgtgtgc cttcactcaa ggaattcaat      60
tcattgagaa aacctgccca ggtgcaacat ctagattcac aatgaacttt ctgattttgt     120
attcatttat tccagctctt gtcatcctag gaatagttgt tttcaaaata agggatcatc     180
tcattagcag gtagtgaaag ccatggctgg gaaaatggaa gtgaagctgc cgactgtgca     240
tgactgctct gaacgtctga atgagagtgc catgtatttt cttcttgac aggacatctc      300 aagtcttta accattaaga ctccatttgt gcctcttgga tccaagcagg ccttgaatgc      360
aatggaagtg gtttatagtc ccttgctctt acaacttgca gggacatgtg gttatttgga     420
aattgtgact gagcggaccc aagaatgtaa ataatattca taaacctatg gg             472

<210> SEQ ID NO 20
<211> LENGTH: 16
<212> TYPE: DNA
<213> ORGANISM: Homo sapiens
<220> FEATURE:
<223> OTHER INFORMATION: 3' splicing site for exon 1
```

```
<400> SEQUENCE: 20
gcgtcaggta aggcag                                                    16

<210> SEQ ID NO 21
<211> LENGTH: 16
<212> TYPE: DNA
<213> ORGANISM: Homo sapiens
<220> FEATURE:
<223> OTHER INFORMATION: 5' splicing site for exon 2

<400> SEQUENCE: 21
cctttaaagc caccgc                                                    16

<210> SEQ ID NO 22
<211> LENGTH: 16
<212> TYPE: DNA
<213> ORGANISM: Homo sapiens
<220> FEATURE:
<223> OTHER INFORMATION: 3' splicing site for exon 2

<400> SEQUENCE: 22
agctcaggta agcttg                                                    16

<210> SEQ ID NO 23
<211> LENGTH: 16
<212> TYPE: DNA
<213> ORGANISM: Homo sapiens
<220> FEATURE:
<223> OTHER INFORMATION: 5' splicing site for exon 3

<400> SEQUENCE: 23
gccccgcagg ctccgg                                                    16

<210> SEQ ID NO 24
<211> LENGTH: 16
<212> TYPE: DNA
<213> ORGANISM: Homo sapiens
<220> FEATURE:
<223> OTHER INFORMATION: 3' splicing site for exon 3

<400> SEQUENCE: 24
cctgcaggtg ggcgcg                                                    16

<210> SEQ ID NO 25
<211> LENGTH: 16
<212> TYPE: DNA
<213> ORGANISM: Homo sapiens
<220> FEATURE:
<223> OTHER INFORMATION: 5' splicing site for exon 4

<400> SEQUENCE: 25
ctcctgcaga gcgaca                                                    16

<210> SEQ ID NO 26
<211> LENGTH: 16
<212> TYPE: DNA
<213> ORGANISM: Homo sapiens
<220> FEATURE:
<223> OTHER INFORMATION: 3' splicing site for exon 4

<400> SEQUENCE: 26
aaggtgggtg cagccc                                                    16

<210> SEQ ID NO 27
<211> LENGTH: 16
```

```
<212> TYPE: DNA
<213> ORGANISM: Homo sapiens
<220> FEATURE:
<223> OTHER INFORMATION: 5' splicing site for exon 5

<400> SEQUENCE: 27
tgcaggtgga ggccgt                                                        16

<210> SEQ ID NO 28
<211> LENGTH: 16
<212> TYPE: DNA
<213> ORGANISM: Homo sapiens
<220> FEATURE:
<223> OTHER INFORMATION: 3' splicing site for exon 5

<400> SEQUENCE: 28
gatcctagta agtggc                                                        16

<210> SEQ ID NO 29
<211> LENGTH: 16
<212> TYPE: DNA
<213> ORGANISM: Homo sapiens
<220> FEATURE:
<223> OTHER INFORMATION: 5' splicing site for exon 6

<400> SEQUENCE: 29
tgctggcaga ggtcat                                                        16

<210> SEQ ID NO 30
<211> LENGTH: 16
<212> TYPE: DNA
<213> ORGANISM: Homo sapiens
<220> FEATURE:
<223> OTHER INFORMATION: 3' splicing site for exon 6

<400> SEQUENCE: 30
ttttcaggta agaggt                                                        16

<210> SEQ ID NO 31
<211> LENGTH: 16
<212> TYPE: DNA
<213> ORGANISM: Homo sapiens
<220> FEATURE:
<223> OTHER INFORMATION: 5' splicing site for exon 7

<400> SEQUENCE: 31
tctggtcagc tctttg                                                        16

<210> SEQ ID NO 32
<211> LENGTH: 16
<212> TYPE: DNA
<213> ORGANISM: Homo sapiens
<220> FEATURE:
<223> OTHER INFORMATION: 3' splicing site for exon 7

<400> SEQUENCE: 32
ttctatagta agtttt                                                        16

<210> SEQ ID NO 33
<211> LENGTH: 16
<212> TYPE: DNA
<213> ORGANISM: Homo sapiens
<220> FEATURE:
<223> OTHER INFORMATION: 5' splicing site for exon 8

<400> SEQUENCE: 33
```

-continued

```
aactttagt ggacct                                              16

<210> SEQ ID NO 34
<211> LENGTH: 16
<212> TYPE: DNA
<213> ORGANISM: Homo sapiens
<220> FEATURE:
<223> OTHER INFORMATION: 3' splicing site for exon 8

<400> SEQUENCE: 34
tcctgaggta agaggc                                             16

<210> SEQ ID NO 35
<211> LENGTH: 16
<212> TYPE: DNA
<213> ORGANISM: Homo sapiens
<220> FEATURE:
<223> OTHER INFORMATION: 5' splicing site for exon 9

<400> SEQUENCE: 35
tgttttcagg agagtg                                             16

<210> SEQ ID NO 36
<211> LENGTH: 16
<212> TYPE: DNA
<213> ORGANISM: Homo sapiens
<220> FEATURE:
<223> OTHER INFORMATION: 3' splicing site for exon 9

<400> SEQUENCE: 36
aatctgtgta agtgcc                                             16

<210> SEQ ID NO 37
<211> LENGTH: 16
<212> TYPE: DNA
<213> ORGANISM: Homo sapiens
<220> FEATURE:
<223> OTHER INFORMATION: 5' splicing site for exon 10

<400> SEQUENCE: 37
catccccagt tcccgt                                             16

<210> SEQ ID NO 38
<211> LENGTH: 17
<212> TYPE: DNA
<213> ORGANISM: Homo sapiens
<220> FEATURE:
<223> OTHER INFORMATION: 3' splicing site for exon 10

<400> SEQUENCE: 38
gctactggtg aggggtt                                            17

<210> SEQ ID NO 39
<211> LENGTH: 16
<212> TYPE: DNA
<213> ORGANISM: Homo sapiens
<220> FEATURE:
<223> OTHER INFORMATION: 5' splicing site for exon 11

<400> SEQUENCE: 39
cttttctagg acgctg                                             16

<210> SEQ ID NO 40
<211> LENGTH: 16
<212> TYPE: DNA
<213> ORGANISM: Homo sapiens
```

```
<220> FEATURE:
<223> OTHER INFORMATION: 3' splicing site for exon 11

<400> SEQUENCE: 40
tcctcaggta agatat                                                  16

<210> SEQ ID NO 41
<211> LENGTH: 16
<212> TYPE: DNA
<213> ORGANISM: Homo sapiens
<220> FEATURE:
<223> OTHER INFORMATION: 5' splicing site for exon 12

<400> SEQUENCE: 41
tttcttaaga aacata                                                  16

<210> SEQ ID NO 42
<211> LENGTH: 16
<212> TYPE: DNA
<213> ORGANISM: Homo sapiens
<220> FEATURE:
<223> OTHER INFORMATION: 3' splicing site for exon 12

<400> SEQUENCE: 42
acttgtggta agtatt                                                  16

<210> SEQ ID NO 43
<211> LENGTH: 16
<212> TYPE: DNA
<213> ORGANISM: Homo sapiens
<220> FEATURE:
<223> OTHER INFORMATION: 5' splicing site for exon 13

<400> SEQUENCE: 43
ccttgacagg cagctc                                                  16

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence:6-His
      epitope tag

<400> SEQUENCE: 44

His His His His His His
  1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence:anti-
      DYKDDDDK epitope tag

<400> SEQUENCE: 45

Asp Tyr Lys Asp Asp Asp Asp Lys
  1               5
```